(12) United States Patent
Eubanks

(10) Patent No.: US 6,617,492 B1
(45) Date of Patent: Sep. 9, 2003

(54) GENETIC MATERIALS FOR TRANSMISSION INTO MAIZE

(76) Inventor: Mary Wilkes Eubanks, 8 Pilton Pl., Durham, NC (US) 27705

(*) Notice: Subject to any disclaimer, the term of this patent is extended or adjusted under 35 U.S.C. 154(b) by 0 days.

(21) Appl. No.: 09/368,869

(22) Filed: Aug. 5, 1999

Related U.S. Application Data

(60) Provisional application No. 60/095,400, filed on Aug. 5, 1998.

(51) Int. Cl.[7] .................. C12N 15/10; C12N 15/29; A01H 1/04; A01H 1/00
(52) U.S. Cl. ............... 800/267; 800/269; 800/320; 800/320.1; 435/6
(58) Field of Search ................ 435/6, 410, 424, 435/430.1; 536/23.1; 800/260, 266, 267, 268, 269, 295, 320.1, 320

(56) References Cited

U.S. PATENT DOCUMENTS

| | | | |
|---|---|---|---|
| PP7,977 P | * | 9/1992 | Eubanks et al. |
| 5,330,547 A | | 7/1994 | Eubanks |
| 5,750,828 A | * | 5/1998 | Eubanks et al. ............ 800/200 |

OTHER PUBLICATIONS

Bates et al. 1974.Proceedings of World–wide maize improvement in the 70's and the role for CIMMYT, Apr. 22–26, El Batan, Mexico. 6pp. CIMMYT, Lonres, Mexico.*
Eubanks et al. 1993.Preliminary data from forage analysis of Tripsacum–diploperennis hyybrid.Maize Genetics Cooperative Newsletter 67:41.*
Eubanks et al. 1995. A cross between two maize relatives; *Tripsacum dactyloides* and *Zea diploperrenis*. Economic Botany 49(2):172–182.*
Eubanks et al. 1997. Molecular analysis of crosses between *Tripsacum dactyloides* and *Zea diploperennis*. Theor. Appl. Genet. 94:707–712.*
Furini et al. 1995. Somatic embryogenesis and plant regenration of maize/Tripsacum hybrids. Maydica 40(2):205–210.*
Kraft et al. 2000. Linkage disequilibrium and fingeprining in sugar beet. Theor. Appl. Genet. 101:323–326.*
Lin et al. Rapid amplification and fixation of new restriction sites inthe ribosomal DNA repeats in the derivatives of a cross between maize and *Tripsacum dactyloides*. Dev. Genetics 6:101–112.*
N.I. Belousova, "Hybridization of maize with Tripsacum in relation to the problem of experimental induction of apomixis." In: Apomixis and Breeding, S. S. Kholchlov (ed.), 1970, pp. 199–220, Amerind Publishing Co. Pvt. Ltd. (translated).

* cited by examiner

Primary Examiner—David T. Fox

(57) ABSTRACT

There is provided a method for transferring novel genetic materials into maize. The method for deriving these new genes is via wide cross hybrid plants produced by crossing two wild relatives of maize, Eastern gamagrass (Tripsacum) and perennial teosinte (*Zea diploperennis*). This invention thus relates to the novel genetic materials in hybrid seed, the hybrid plant produced by the seed and/or tissue culture, variants, mutants, modifications, and cellular and molecular components of Tripsacum-perennial teosinte hybrids, and the hybrid seed, the hybrid plant produced by the seed and/or tissue culture, variants, mutants, modifications, and cellular and molecular components of (maize X Tripsacum-perennial teosinte) and/or (Tripsacum-perennial teosinte X maize). In particular this invention is directed to the ability to transfer de novo nucleotide sequences and novel alleles from Tripsacum to maize for use in genetic analyses and selection of novel genotypes with enhanced agronomic traits such as insect and disease resistance, drought tolerance, cold tolerance, tolerance to water-logging, apomixis, totipotency, perennialism, as well as adaptation to adverse soil conditions and a carbon dioxide enriched atmosphere via (maize X Tripsacum-perennial teosinte) hybrids in corn improvement programs.

1 Claim, 1 Drawing Sheet

200
GENETIC MATERIALS FOR TRANSMISSION INTO MAIZE

RELATED U.S. APPLICATIONS

This application claims the benefit of U. S. Provisional Application No. 60/095,400 filed on Aug. 5, 1998.

FEDERALLY SPONSORED RESEARCH

Part of the research on which this patent application is based was funded by National Science Foundation Grants No. 9660146 and 9801386.

FIELD OF THE INVENTION

This invention relates generally to the fields of molecular genetics and plant breeding. More particularly, it relates to a means of moving novel, stably inherited, variant forms of DNA into maize (*Zea mays L.*), also referred to as corn in the United States. These novel DNA sequences, derived from intergeneric hybridization between Eastern gamagrass (*Tripsacum dactyloides L.*) and perennial teosinte (*Zea diploperennis Iltis*, Doebley and Guzmán), provide unique markers for assisting selection of desirable traits in plant breeding programs, for detection of target DNA sequences in genetic analyses, and for the identification of new genes for corn improvement that may enhance resistance to insect pests and diseases, drought stress tolerance, cold tolerance, perennialism, grain yield, totipotency, apomixis, improved root systems, tolerance of water-logged soils, tolerance of high-aluminum and acidic soils, improved grain quality, enhanced forage quality, and adaptability to a CO2 enriched atmosphere.

BACKGROUND OF THE INVENTION

Molecular Genetics. Genetics is the study of genes and heritable traits in biological organisms. In plant breeding, the goal of molecular genetics is to identify genes that confer desired traits to crop plants, and to use molecular markers (DNA signposts that are closely associated with specific genes) to identify individuals that carry the gene or genes of interest in plants (Morris 1998), to determine the DNA sequences and characterize gene expression and function. A genetic marker is a variant allele that is used to label a biological structure or process throughout the course of an experiment. Variants in DNA and proteins are used as markers in molecular genetics. Genetic analysis of molecular variants can identify a particular gene that is important for a biological process. Mutation is the process whereby nucleotide sequences and genes change from the reference form generally designated wild type to a different form, and mutants are the source of variant genotypes in genetic analysis that allow selection of new phenotypes (Griffiths et al. 1993). Mutations occur at the level of a specified nucleotide sequence, the gene (i.e. DNA sequence), or the chromosome (i.e. the hereditary package in which units of DNA containing specific nucleotide sequences and genes are supercoiled with proteins). In a genetic mutation, the nucleotides that comprise the wild type allele of a gene (i.e. reference form that exists at a particular locus) is altered. In chromosome mutations, segments of chromosomes, whole chromosomes, or entire sets of chromosomes change via inversion, translocation, fusions and deletions.

In general, mutations are very rare, and most newly formed mutations are deleterious. Data on mutation frequencies for seven genes in maize provides a baseline indicating the rarity of mutations in maize (Stadler 1951). Mutation frequency ranged from 0.000492% (i.e. 492 mutants out of a million gametes) in the red color(R) gene; 0.000106% (i.e. 106 out of a million) for the inhibitor of R (I) gene; 0.000011% (i.e. 11 out of a million) for the purple aleurone (Pr) gene; 0.0000024% (i.e. 2.4 out of a million) for the starchy (Su) gene; 0.0000022% (i.e. 2.2 out of a million) for the yellow color (Y) gene; 0.0000012% (i.e. 1.2 out of a million) for the normal kernel (Sh) gene, and 0% (i.e. 0 out of a million for the waxy gene (Wx).

Because spontaneous mutations are rare, geneticists and plant breeders typically use mutagens (i.e. agents such as chemicals and radiation to increase the frequency of mutation rates) to obtain variant forms that can be used in genetic analysis and selection of new varieties. Another method of inducing mutagenesis in maize is transposon tagging whereby a maize line is crossed with a line containing one of the three systems of transposable elements found in maize. When a transposable element inserts into a gene, it causes a mutation. The reported mutation frequencies for transposable element mutator lines varies from 1 in a thousand to 1 in a million (Chomet 1994). To find a mutation using one of these mutagenic lines, a breeder must screen a minimum of 100,000 progeny.

Plant Breeding. Conventional plant breeding is the science that utilizes crosses between individuals with different genetic constitutions. The resulting recombination of genes between different lines, families, species, or genera produces new hybrids from which desirable traits are selected. Plant breeding is achieved by controlling reproduction. Since maize is a sexually reproducing plant, techniques for controlled pollination are frequently employed to obtain new hybrids. Controlling reproduction in maize involves continually repeating two basic procedures: (1) evaluating a series of genotypes, and (2) self-pollinating or crossing among the most superior plants to obtain the next generation of genotypes or progeny. Controlled pollinations in maize utilize two procedures: (1) detasseling, and (2) hand pollination.

Maize is a monoecious grass that has separate male and female flowers on the same plant. The male or staminate flowers produce pollen in the tassel at the apex of the maize stalk, and the female or pistillate flowers that produce the grain when pollinated are borne laterally in leaf axils tangential to the stalk. Pollination is accomplished by transfer of pollen from the tassel to silks which emerge from the axillary pistillate ears. Since maize is wind-pollinated, controlled pollination in which pollen collected from the tassel of one plant and transferred by hand to the silks of the same or another plant, is a technique used in maize breeding. The steps involved in making controlled crosses and self-pollinations in maize are standard practice (Neuffer 1982) and are as follows: (1) the ear emerging from the leaf shoot is covered with an ear shoot bag one or two days before the silks emerge to prevent contamination by stray pollen; (2) prior to making a pollination, the ear shoot bag is quickly removed and the silks cut with a knife to form a short brush, then the bag is immediately placed back over the ear; (3) also prior to making a pollination, the tassel is covered with a tassel bag to collect pollen; (3) on the day crosses are made, the tassel bag with the desired pollen is carried to the plant for crossing, the ear shoot bag is removed and the pollen dusted on the silk brush, the tassel bag is then fastened in place over the pollinated shoot to protect the developing ear.

*Zea diploperennis* (hereafter referred to as diploperennis), is a diploid perennial teosinte and a wild relative of maize endemic to the mountains of Jalisco, Mexico. Diploperennis is in the same genus as maize, has the same chromosome number (2n=20), and can hybridize naturally with it.

Tripsacum is a polyploid, rhizomatous perennial grass that is a more distant wild relative of maize and has a different chromosome number (x=18, 2n=36 or 2n=72). Tripsacum is not know to naturally form fertile hybrids with maize or the wild Zeas. The progeny of (maize X Tripsacum) obtained by artificial methods have ten maize chromosomes and either 18 or 36 Tripsacum chromosomes and are male sterile. Female fertility can be partially restored using special techniques that eliminate most of the Tripsacum chromosomes (Mangelsdorf 1974). Plants obtained by crossing Tripsacum and maize (*Zea mays L.*) employing Tripsacum as the pollen donor have unreduced gametes with a complete set of Zea chromosomes and a complete set of Tripsacum chromosomes. There is one report of a successful reciprocal cross in which Tripsacum was pollinated by maize that required embryo culture techniques to bring the embryo to maturity, and the plants were sterile (Farquharson 1957). Maize-Tripsacum hybrids have been crossed with teosinte to created a trigenomic hybrid that has a total of 38 chromosomes; 10 from maize, 18 from Tripsacum and 10 from teosinte. The resulting trigenomic plants were all male sterile and had a high degree of female infertility (Mangelsdorf 1974; Galinat 1986).

Based on known crossability relationships between Zea and Tripsacum and the results of prior crosses between them, the success of the crosses between *Zea diploperennis* and Tripsacum resulting in viable, fully fertile plants with chromosome numbers of 2n=20 (Eubanks 1995, 1997) could not have been predicted. Reduction in chromosome number in the interspecific crosses was unexpected based on prior art. The fertility of plants resulting from the cross made both ways with Tripsacum as pollen donor and pollen recipient was also unexpected based on prior art.

Although the base chromosome numbers of Tripsacum and *Zea diploperennis* are different, x=10 in Zea and x=18 in Tripsacum, their respective total chromosome lengths are almost equal. The total length of the 18 *Tripsacum dactyloides* chromosomes is 492.5$\mu$ (Chandravadana et al. 1971), and the total length of the 10 *Zea diploperennis* chromosomes is 501.64$\mu$ (Pasupuleti and Galinat 1982). It is not easy to obtain a hybrid plant when crossing Tripsacum and diploperennis. Hundreds of pollinations are required to obtain a viable seed, and approximately half of seedlings that germinate die soon after germination. However, as evidenced by cross fertility and chromosome number, when precise alignments occur between homologous regions of the chromosomes of Tripsacum and diploperennis there is a sufficient degree of pairing to occasionally enable the rare and unexpected success of this cross.

The unexpected fertility of Tripsacum-perennial teosinte hybrids, and their cross-fertility with maize, are of great value because they provide opportunity for directly crossing the recombined intergeneric germplasm with maize. In addition to providing a genetic bridge for importing Tripsacum genes into maize, *Tripsacum-diploperennis* hybrids provide a mechanism for importing any new Tripsacum genes not found in maize or the wild Zeas, and any de novo genetic material that arises from these wide species crosses into maize using traditional plant breeding techniques.

DNA fingerprinting has revealed that new Tripsacum alleles not found in maize or the wild Zeas and de novo sequences newly created via the wide cross are stably inherited in the progeny of succeeding generations and can be conferred to maize by crossing maize with *Tripsacum-diploperennis* containing de novo nucleotide sequences and alleles unique to Tripsacum. For purposes herein, de novo genetic material refers to regions where new allelic forms of DNA sequences are repeatedly and reliably created whenever crosses between Tripsacum and *Zea diploperennis* produce viable, fertile plants.

Feasibility has been demonstrated in plants derived from crossing *Tripsacum-diploperennis* with maize that exhibit resistance to western corn rootworm (*Diabrotica virgifera* Le Conte) and corn borer, tolerance to drought, and have properties of perennialism. Investigation and characterization of association with other traits such as response to high levels of atmospheric $CO_2$ are in process.

References Cited

U.S. PATENT DOCUMENTS

| | | |
|---|---|---|
| 4,545,146 | October 1985 | Davis |
| 4,627,192 | December 1986 | Fick |
| 4,684,612 | August 1989 | Hemphill et al |
| 4,737,596 | April 1988 | Seifert et al. |
| 4,837,152 | June 1989 | Hemphill and Warshaw |
| 5,059,745 | October 1991 | Foley |
| PP 6,906 | July 1989 | Eubanks |
| PP 7,977 | September 1992 | Eubanks |
| 5,330,547 | July 1994 | Eubanks |
| PP 9,640 | September 1996 | Eubanks |
| 5,750,828 | May 1998 | Eubanks |

Other Publications

Chaganti, R. S. K. 1965. Cytogenetic studies of maize-Tripsacum hybrids and their derivatives. Harvard Univ. Bussey Inst., Cambridge, Mass.

Chandravadana, P., W. C. Galinat and B. G. S. Rao. 1971. A cytological study of *Tripsacum dactyloides*. J. Hered. 62:280–284.

Chomet, P. S. 1994. Transposon tagging with Mutator. In M. Freeling and V. Walbot (eds.), The Maize Handbook, Springer-Verlag, New York.

Cohen, J. I. and W. C. Galinat. 1984. Potential use of alien germplasm for maize improvement. Crop Sci. 24:1011–1015.

Curtis, H. and N. S. Barnes. 1989. Biology. Worth Publishers, Inc. New York, N.Y.

Eubanks, M. W. 1995. A cross between two maize relatives: *Tripsacum dactyloides* and *Zea diploperennis* (Poaceae). Econ. Bot: 49:172–182.

Eubanks, M. W. 1997. Molecular analysis of crosses between *Tripsacum dactyloides* and *Zea diploperennis* (Poaceae). Theor. Appl. Genet. 94:707–712.

Farquharson, L. I. 1957. Hybridization of Tripsacum and Zea. J. Heredity 48:295–299.

Galinat, W. C. 1974. Intergenomic mapping of maize, teosinte and Tripsacum. Evolution 27:644–655.

Galinat, W. C. 1977. The origin of corn. In G. F. Sprague (ed.). Corn and Corn Improvement. Amer. Soc. Agronomy, Madison, Wis.

Galinat, W. C. 1982. Maize breeding and its raw material. In W. L. Sheridan (ed.) Maize for Biological Research. University Press, Grand Forks, N.Dak.

Galinat, W. C. 1986. The cytology of the trigenomic hybrid. Maize Genetics Newsletter 60:133.

Gardiner, J. E. H. Coe, S. Melia-Hancock, D. A. Hoisington and S. Chao. 1993. Development of a core RFLP map in maize using an immortalized $F_2$ population. Genetics 134:917–930.

Griffiths, A. J. F., J. H. Miller, D. T. Susuki, R. C. Lewin, and W. M. Gelbart. 1993. *An Introduction to Genetic Analysis*, 5th edition. W.H. Freeman and Co., New York.

Helentjaris, T., M. Slocum, S. Wright, A. Schaefer and J. Nienhuis. 1986. Construction of genetic linkage maps in maize and tomato using restriction fragment length polymorphisms. Theor. Appl. Genet. 72:761–769.

Jeffreys, A. J., N. J. Royle, W. Wilson and Z. Wong. 1988 Spontaneous mutation rates to new length alleles at tandem-repetitive hypervariable loci in human DNA. Nature 332:278–281.

Kindiger, B. and J. B. Beckett. 1990. Cytological evidence supporting a procedure for directing and enhancing pairing between maize and Tripsacum. Genome 33:495–500.

Kresovich, S., W. F. Lamboy, A. K. Szewc-McFadden, J. R. McFerson, and P. L. Forsline. 1993. Molecular diagnostics and plant genetic resources conservation. Agbiotech News and Information 5(7):255–258.

Lewin, B. 1997. Genes V. Oxford University Press, Oxford, UK.

Maguire, M. P. 1961. Divergence in Tripsacum and Zea chromosomes. Evolution 15:393–400.

Maguire, M. P. 1963. Chromatid interchange in allodiploid maize-Tripsacum hybrids. Can. J. Genet. Cytol. 5:414–420.

Mangelsdorf, P. C. 1974. Corn: Its origin, evolution and improvement. Harvard Univ. Press, Cambridge, Mass.

Melchinger, A. E., M. M. Messmer, M. Lee, W. L. Woodman, and K. R. Lamkey. 1991. Diversity and relationships among U.S. maize inbreds revealed by restriction fragment length polymorphisms. Crop Science 31:669–678.

Messmer, M. M., A. E. Melchinger, R. Herrmann, and J. Boppenmaier. 1993. Relationships among early European maize inbreds: II. Comparison of pedigree and RFLP data. Crop Science 33:944–950.

Morris, M. L., Ed. 1998. *Maize Seed Industries in Developing Countries*. Lynne Rienner Publishers, Inc., Boulder, Colo.

Neuffer, M. G. 1982. Growin maize for genetic purposes. In W. L. Sheridan (ed.) Maize for Biological Research. University Press, Grand Forks, N.Dak.

Neuffer, M. G., E. H. Coe and S. R. Wessler. 1997. Mutants of Maize. Cold Spring Harbor Laboratory Press, New York.

Pasupuleti, C. V. and W. C. Galinat. 1982. *Zea diploperennis* I. Its chromosomes and comparative cytology. Heredity 73:168–170.

Poehlman, J. M. 1986. Breeding Field Crops. 3rd ed. AVI Publ. Co., Inc., Westport, Conn.

Reeves, R. G. and A. J. Bockholt. 1964. Modification and improvement of a maize inbred by crossing it with Tripsacum. Crop Sci. 4:7–10.

Smith, O. S. and J. S. C. Smith. 1992. Measurement of genetic diversity among maize hybrids; a comparison of isozymic, RFLP, pedigree, and heterosis data. Maydica 37:53–60.

Stadler, L. J. 1951. Spontaneous mutation in maize. Cold Spring Harbor Symp. Quant. Biol. 16:49–63.

Tantravahi, 1968. Cytology and crossability relationships of Tripsacum. Harvard Univ. Bussey Inst., Cambridge, Mass.

SUMMARY OF THE INVENTION

In one embodiment of the invention, there is provided a method for conferring novel genetic materials into maize. In the first step of the method, a Tripsacum plant is pollinated by pollen from a perennial teosinte plant by controlled pollination technique, or vice versa, a perennial teosinte plant is pollinated by pollen from a *Tripsacum dactyloides* plant. The resulting intergeneric hybrids derived in step 1 are fully fertile and cross-fertile with maize. The hybrid plants are characterized by their utility as a genetic bridge to transfer novel genetic materials into maize and their unexpected chromosome number of 2n=20 instead of the expected 2n=28 or 2n=46 if a full, unmodified complement of perennial teosinte haploid chromosomes (n=10) and diploid Tripsacum (n=18) or tetraploid Tripsacum (n=36) chromosomes were transmitted to the resulting hybrid progeny.

In another embodiment of the invention, in step 2 of the method, the intergeneric hybrid plant (Tripsacum X perennial teosinte) or (perennial teosinte X Tripsacum) is crossed with maize by controlled pollination. In the cross, the pollen of (Tripsacum X perennial teosinte) or (perennial teosinte X Tripsacum) is transferred to maize silks, or maize pollen is transferred to the silks of (Tripsacum X perennial teosinte) or (perennial teosinte X Tripsacum). This invention relates to hybrid seed, hybrid plants produced by the seed and/or tissue culture, variants, mutants, modifications, and cellular and molecular components of the hybrid plants that contain novel genetic materials derived from (Tripsacum X perennial teosinte) or (perennial teosinte X Tripsacum).

In another embodiment of the invention, in step 3 of the method, the trigeneric hybrid plant obtained from crossing (Tripsacum X perennial teosinte) or (perennial teosinte X Tripsacum) with maize by controlled pollination as described in step 2, is backcrossed to maize or (Tripsacum X perennial teosinte) or (perennial teosinte X Tripsacum). In the backcross, the pollen of the trigeneric hybrid plant is transferred to the silks of one of the original parents (Tripsacum X perennial teosinte) or (perennial teosinte X Tripsacum) or maize. This invention relates to hybrid seed, hybrid plants produced by the seed and/or tissue culture, variants, mutants, modifications, and cellular and molecular components of the backcrossed hybrid plants that contain novel genetic materials derived from (Tripsacum X perennial teosinte) or (perennial teosinte X Tripsacum).

In another embodiment of the invention, there is provided plants and plant tissues produced by the method of crossing maize with a *Tripsacum-diploperennis* hybrid that contain novel genetic materials and exhibit beneficial agronomic traits. For example, these plants may contain novel genes for such traits as pest and pathogen resistance, drought tolerance, cold tolerance, water-logging tolerance, improved grain quality, improved forage quality, totipotency, perennialism, tolerance to acidic soils, tolerance to high-aluminum soils, enhanced adaptability in a carbon dioxide enriched environment and can be employed in recurrent selection breeding programs to select for hybrid maize that exhibit such traits.

For the purposes of this application, the following terms are defined to provide a clear and consistent description of the invention.

Allele. One of the different forms of a gene that can exist at a single locus.

Autoradiography. A process in which radioactive materials are incorporated into cellular components, then placed next to a film or photographic emulsion to produce patterns on the film that correspond to the location of the radioactive compounds within the cell.

Electrophoresis. A technique for separating the components of a mixture of molecules (proteins, DNAs, or RNAs) in an electric field within a gel matrix.

Genetic markers. Alleles used as experimental probes to keep track of an individual, a tissue, a cell, a nucleus, a chromosome, or a gene.

Gene. The fundamental physical and functional unit of heredity that carries information from one generation to the next. The plant gene is "a DNA sequence of which a segment is regularly or conditionally transcribed at some time in either or both generations of the plant. The DNA is understood to include not only the exons and introns of the structural gene but the cis 5' and 3' regions in which a sequence change can affect gene expression" (Neuffer, Coe and Wessler 1997).

Genotype. The allelic composition of a cell—either of the entire cell or, more commonly, for a certain gene or a set of genes of an individual.

Hybrid plant. An individual plant produced by crossing two parents of different genotypes or germplasm backgrounds.

Locus. The place on a chromosome where a gene is located.

Molecular genetics. The study of the molecular processes underlying gene structure and function.

Mutagen. An agent that is capable of increasing the mutation rate.

Mutation. (1) The process that produces nucleotide sequences, genes, genetic elements, or chromosomes differing from the wild-type. (2) The nucleotide sequences, genes, genetic elements, or chromosomes that result from such a process.

Plant breeding. The application of genetic analysis to development of plant lines better suited for human purposes.

Probe. Defined nucleic acid segment that can be used to identify specific molecules bearing the complementary DNA or RNA sequence, usually through autoradiography.

Restriction enzyme. An endonuclease that will recognize specific target nucleotide sequences in DNA and cut the DNA at these points; a variety of these enzymes are known and they are extensively used in genetic engineering.

RFLP. Refers to restriction fragment length polymorphism that is a specific DNA sequence revealed as a band of particular molecular weight size on a Southern blot probed with a radiolabelled RFLP probe and is considered to be an allele of a gene.

Southern blot. Transfer of electrophoretically separated fragments of DNA from the gel to an absorbent surface such as paper or a membrane which is then immersed in a solution containing a labeled probe that will bind to homologous DNA sequences.

Totipotency. The ability of a cell to proceed through all the stages of development and thus produce a normal adult.

Wild type—refers to a reference and it can mean an organism, set of genes, gene or nucleotide sequence. For purposes herein the wild type refers to the parents of hybrid progeny.

DETAILED DESCRIPTION OF THE INVENTION

Figure 1:
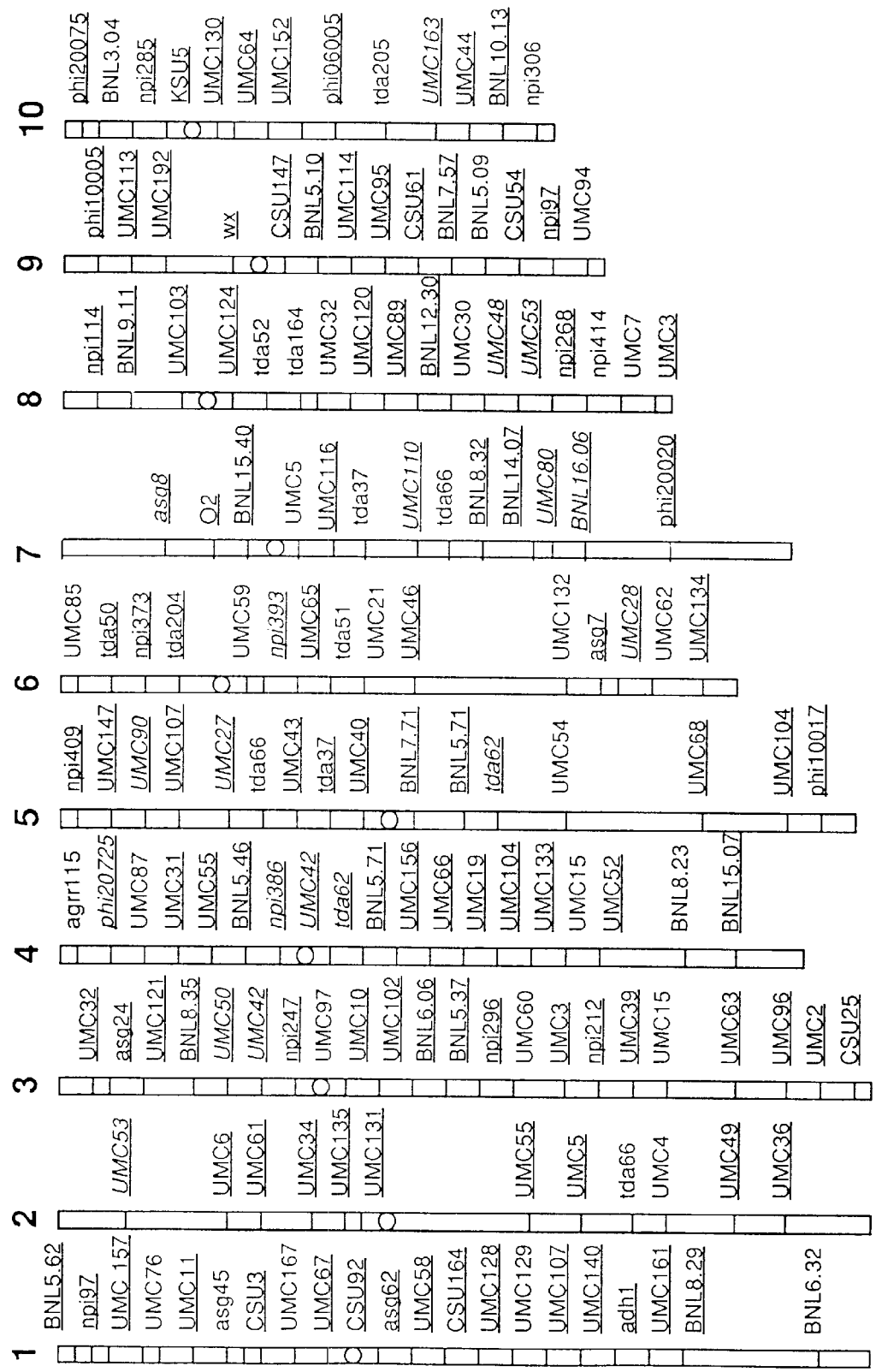
FIG. 1 is a schematic drawing of the 10 linkage groups of maize. The open circles represent approximate positions of the centromeres. The labelled lines indicate positions where the probes used to DNA fingerprint hybrid plants derived from crossing *Tripsacum dactyloides* and *Zea diploperennis*, as well as maize plants crossed with the *Tripsacum-diploperennis* bridging species are located on maize chromosomes. Molecular markers that reveal loci where stable, heritable de novo alleles are underscored, and loci where stable, heritable new alleles from Tripsacum that are not found in maize or the wild Zeas are italicized.

The principles and techniques used to identify de novo genetic material and novel Tripsacum alleles are central to molecular genetics and are commonly used to fingerprint crop varieties (Kresovich et al. 1993). First DNA is extracted and isolated from plant samples; then the DNA is cut into fragments using restriction enzymes that cut at precise nucleotide sequences; the fragments are then separated by size, i.e. molecular weight, on an agarose gel by electrophoresis; the DNA is then denatured, i.e. separated into single strands, and transferred to a nitrocellulose filter which binds single-stranded but not double-stranded DNA, a method referred to as Southern blotting. The restriction fragments are immobilized on the filter in a pattern that mirrors their positions in the agarose gel. The membrane is then incubated in a solution containing multiple copies of a radiolabeled probe for a particular DNA sequence that has been mapped to a certain chromosomal locus or loci in the maize genome; the probe hybridizes to homologous DNA sequences, and the distinctive banding pattern formed by a particular restriction enzyme/probe combination in any individual plant can be visualized on an autoradiograph. The banding patterns, which resemble a bar code, precisely identify the genotype of individual plants. The patterns formed by specific restriction enzyme/probe combinations are referred to as restriction fragment length polymorphisms (RFLPs), and they provide sufficient information to distinguish between plants whose genetic composition may differ slightly. These genetic fingerprinting techniques permit the unambiguous identification of genotypes (Melchinger et al. 1991; Messmer et al. 1993). Fingerprinting profiles are routinely used for genetic identity analysis to classify closely related materials, estimate genetic distances between such materials, determine paternity, and complement conventional pedigree records in commercial hybrid production (Smith and Smith 1992).

Since maize is a diploid organism, the progeny of maize hybrids inherit one allele for a trait from one parent and another allele for that trait from the other parent. In the DNA fingerprint of a single gene that is not duplicated elsewhere in the genome, if the progeny inherits the same allele for a trait from both parents, it is homozygous for that trait and a single band will be present on the DNA profile using a molecular probe that maps to the specific region of the particular chromosome to which the trait being investigated has been mapped. If the progeny inherits different alleles from each parent plant, it will be heterozygous at that locus and two bands will be detected on the autoradiograph, one band from one parent and a different band from the other parent. At more complex loci involving gene duplication, multiple bands can be seen. In general, the offspring of two parents can be identified by comparing the banding pattern profile because the progeny exhibit a combination of bands from both parents. Sometimes, however, the progeny of known parentage exhibit a band or bands that are not found in either parent. Such de novo bands arise from mutable or recombinant events that give rise to changes in the nucleotide sequences such that the banding pattern is different from both of its parents (Griffiths et al. 1993). Such mutant or novel rearrangements in the genetic material are revealed by comparative analysis of the banding patterns of the parent plants and hybrid progeny. Bands present in the progeny not found in either parent indicate regions of the genome where novel genetic material has arisen, i.e. mutations have occurred.

As stated above, mutations are rare, and in most cases are deleterious. Broadly speaking among all organisms, mutation rates vary and they range from 1 in 1,000 to 1 in 1,000,000 gametes per generation depending on the gene involved (Curtis and Barnes 1989). For example, each human with approximately 100,000 genes is expected to carry 2 mutant alleles. The Tripsacum-perennial teosinte hybrids are unprecedented in that their DNA fingerprints reveal they have an extremely high mutation rate with de novo alleles at 133 out of 173 loci. Furthermore, de novo alleles are stably inherited in succeeding generations of *Tripsacum-diploperennis* progeny and of maize X *Tripsacum-diploperennis* progeny. In addition to the rarity and usual deleterious effect of mutations, a basic biological tenet is that mutations occur at random or by chance (Lewin 1997). In a study of spontaneous mutation rates to new length alleles at tandemly repeated loci in human DNA (Jeffreys et al. 1988) mutations arose sporadically and there was no clustering of mutations within a family. Siblings never shared a common mutant allele. Therefore, it is unexpected that the same mutations would recur among siblings or among hybrids of different parentage. Thus it is remarkable and unexpected that the same de novo alleles are repeatedly found in hybrid progeny derived from crossing different Tripsacum and perennial teosinte parent plants, and that those same de novo alleles are stably inherited in crosses between Tripsacum-perennial teosinte hybrids and maize. These de novo alleles provide a rich new source of variant genetic material for selection in corn improvement.

In molecular assays performed by Linkage Genetics, Salt Lake City, Utah, and Biogenetics, Inc., Brookings, S.Dak., DNA was isolated from different $F_1$, $F_2$ and $F_3$ hybrids between *Tripsacum dactyloides* and *Zea diploperennis*, the parents of these hybrids, W64A and B73 maize inbred lines, as well as $F_1$, $F_2$, $F_3$ and $F_4$ hybrids between maize and *Tripsacum-diploperennis*. The protocol for DNA isolation, restriction enzyme digestion, Southern blotting, probe hybridization, and analysis of autoradiographs has been described by Helentjaris et al. (1986). Internal standards of known molecular weights and a ladder were included in the gels to facilitate accuracy of describing the banding patterns in terms of molecular weights of alleles. Five different *Tripsacum-diploperennis* hybrids have been fingerprinted: (1) Sun Dance, *Zea diploperennis* 3-7 X *Tripsacum dactyloides* (2n=72); (2) Tripsacorn, *Tripsacum dactyloides* (2n=72) X *Zea diploperennis* 3-3; (3) Sun Star, *Zea diploperennis* 2-4 X *Tripsacum dactyloides* (2n=36); (4) Sun Devil, *Tripsacum dactyloides* (2n=72) X *Zea diploperennis*; (5) The maize inbred lines W64A and B73 were crossed with some of the above *Tripsacum-diploperennis* hybrids.

Total genomic DNA from individuals in some of the above listed lines was digested with from one to four different restriction enzymes, EcoRI, EcoRV, HindIII, and BamI, transferred to Southern blots, and probed with 173 publicly available DNA markers which include a majority of maize nuclear DNA probes mapped to the ten linkage groups of maize (Gardiner et al. 1993), six maize mitochondrial probes, and some Tripsacum (tda) probes for which the loci have not yet been mapped to the maize genome. The molecular markers on the genetic linkage map of maize were mapped by recombinational analyses based on proof of the identity of a clone. Thus each locus represents a gene based on clone identification (Neuffer, Coe and Wessler 1997). The 173 molecular markers that were employed in DNA fingerprinting of parent species, *Tripsacum-diploperennis* hybrids, and maize X *Tripsacum-diploperennis* are listed in Table 1. FIG. 1 depicts the orders and approximate locations of the mapped probes on the ten maize chromosomes (cf. Neuffer, Coe and Wessler 1997). A large number of the probes reveal bands that are not present in either parent of a particular progeny. These de novo bands signal loci where mutations occurred in the process of intergeneric hybridization and they are underscored in Table 1 and FIG. 1. There are also loci where Tripsacum alleles are present in *Tripsacum-diploperennis* hybrids that are not present in maize or the wild Zeas. Thus these are novel alleles that can now be conferred to maize via the Tripsacum-perennial teosinte genetic bridge and they are italicized in Table 1 and FIG. 1.

Table 2 lists the approximate size, i.e. molecular weight, of each de novo band per restriction enzyme/probe combination that has arisen as a result of the mutagenic effect of the wide cross hybridization. Table 3 lists approximate size of the novel Tripsacum alleles not found in maize or the wild Zeas that can now be conferred to maize via *Tripsacum-diploperennis* hybrid lines according to restriction enzyme/probe combination.

Tables 4 identifies the mutant nucleotide sequences, and specifies their inheritance in Tripsacum-diploperennis hybrids and eight exemplary (maize X *Tripsacum-diploperennis*) lines. Table 5 identifies the nucleotide sequences that are alleles from the Tripsacum parents employed in producing the *Tripsacum-diploperennis* hybrids and specifies their inheritance in the *Tripsacum-diploperennis* hybrids and eight exemplary (maize X *Tripsacum-diploperennis*) lines. In order to determine which Tripsacum alleles are present in *Tripsacum-diploperennis* hybrids that are not present in other Zeas, 5 to 13 individuals from populations of two modern maize inbred lines, B73 and W64A, four indigenous Latin American maize races, Nal Tel (Yuc7), Chapalote (Sin), Pollo (Col 35 ICA), and Pira (PI44512), and the six wild Zeas, *Z. mexicana* (PI566683 and PI566688), *Z. parviglumis* (PI384061 and PI331785), *Z. luxurians* (PI306615), *Z. huehuetenangensis* (Ames21880), *Z. diploperennis* and *Z. perennis* (Ames 21875), were DNA fingerprinted with the probes in Table 1 and FIG. 1. The nucleotide sequences are identified by probe/restriction enzyme/probe and molecular weight.

The novel genetic materials, including de novo alleles and new alleles from Tripsacum, that are not found in maize or the wild Zeas, have been shown to be stably inherited in three generations of *Tripsacum-diploperennis* hybrids, and four generations of *Tripsacum-diploperennis* hybrids that were crossed with maize. The new Tripsacum alleles and mutated nucleotide sequences, their heritability in succeeding generations of *Tripsacum-diploperennis* hybrids, and their transmissibility to maize is unprecedented and unexpected based on prior art. These novel DNA sequences have utility for genetic analysis of Zea, and selection of new variant alleles that may enhance traits such as insect and disease resistance, drought stress tolerance, cold tolerance, perennialism, increased grain yield, totipotency, apomixis, better root systems, tolerance of water-logged soils, tolerance of high-aluminum and acidic soils, improved grain quality, and improved forage quality. New traits derived from these mutations or novel Tripsacum genes can be successfully employed in recurrent selection breeding programs for maize improvement.

The method of the invention is performed by crossing *Tripsacum dactyloides* and *Zea diploperennis*. The crosses are performed using standard plant breeding techniques for controlled pollinations known in the art. Some *Tripsacum-diploperennis* hybrid plants which are perennials that reproduce asexually as well as by seed have been described in the following plant patents: PP No. 9,640 issued Sep. 3, 1996; PP No. 7,977 issued Sep. 15, 1992, and PP No. 6,906 issued Jul. 4, 1989. U.S. Pat. No. 5,330,547 issued Jul. 19, 1994, and U.S. Pat. No. 5,750,828 issued May 12, 1998, describe a method for employing *Tripsacum-diploperennis* hybrids to confer corn rootworm resistance to maize.

The present invention provides a method of obtaining novel genetic materials, including de novo mutant nucleotide sequences and new alleles from Tripsacum that are not found in maize or the wild Zeas, by producing hybrid plant seeds comprising the steps of (a) pollinating a Tripsacum species (e.g. *Tripsacum dactyloides*) female parent with pollen from a perennial teosinte species (e.g. *Zea diploperennis*) male parent, or of pollinating a perennial teosinte species (e.g. *Zea diploperennis*) female parent with pollen from a Tripsacum species (e.g. *Tripsacum dactyloides*), to produce seed; then (b) harvesting the seed produced.

This method produces a hybrid seed from which a hybrid plant containing novel genetic materials can be grown, and from hybrid plants containing novel genetic material tissue cultures can be made. Additionally, pollen produced by the hybrid plant containing novel genetic material can be collected.

The term "plant" as used in this application refers to the whole plant as well as its component parts, e.g., flowers, roots, fruits, stems, rhizomes, pollen.

The present invention further provides a method of producing hybrid maize seed containing novel genetic materials comprising the steps of (a) crossing a Tripsacum pollen recipient plant with a perennial teosinte pollen donor to plant produce (Tripsacum X perennial teosinte), or a perennial teosinte pollen recipient plant with a Tripsacum pollen donor plant (perennial teosinte X Tripsacum), to produce hybrid seed; then (b) growing a (Tripsacum X perennial teosinte) or (perennial teosinte X Tripsacum) hybrid plant from said seed to maturity; then (c) crossing said (Tripsacum X perennial teosinte) or (perennial teosinte X Tripsacum) hybrid plant with either a maize pollen recipient or maize pollen donor plant to produce seed and (d) harvesting the seed produced.

This method results in the production of hybrid maize seed and hybrid maize plants containing novel genetic materials, from which tissue cultures can be made. Plant breeding techniques and tissue culture techniques as described herein are known, and may be carried out in the manner known to those skilled in the art. See, for example, U.S. Pat. No. 4,737,596 to Seifert et al. entitled "Hybrid Maize Plant and Seed"; U.S. Pat. No. 5,059,745 to Foley entitled "Hybrid Maize Line LH195"; U.S. Pat. No. 4,545,146 to Davis entitled "Route to Hybrid Soybean Production"; U.S. Pat. No. 4,627,192 to Fick entitled "Sunflower Products and Methods for their Production", and U.S. Pat. Nos. 4,837,152 and 4,684,612 entitled "Process for Regenerating Soybeans"; U.S. Pat. Nos. 5,330,547 and 5,750,828 to Eubanks entitled "Methods and Materials for Conferring Tripsacum Genes in Maize."

In Tripsacum inflorescences, the staminate (i.e. male) flowers and pistillate (i.e. female) flowers are produced on a single spike with the male flowers subtended by the female. When Tripsacum sends out the inflorescence, the staminate flowers are broken off leaving only the female flowers on the spike which are then covered with a pollinating bag, i.e. standard ear shoot bag for maize, to protect them from contamination by unwanted pollen. Perennial teosinte male and female flowers occur on separate parts of the plant. The staminate flowers are borne in the tassel which emerges at the apex of the culm; whereas, the pistillate flowers occur in single-rowed spikes borne on lateral branches of the culm. When perennial teosinte produces its tassels, they are covered with a pollinating bag. When they start shedding pollen, the bag is removed and pollen taken to pollinate the Tripsacum plants. At that time, the bags covering the Tripsacum pistillate flowers are removed and the perennial teosinte pollen shaken out of the bag onto the silks. The Tripsacum inflorescence is covered again with a pollinating bag immediately after pollination and the bag is stapled so that it remains on the spike until the seed has matured. Upon maturity, approximately 45 days later, the seed is harvested. Once mature seed from the cross has been obtained, it is planted, and the plants from seed that germinates are grown in a growth chamber, greenhouse or the field. Controlled crosses are best made in a greenhouse or growth chamber where plants are kept isolated to prevent cross contamination and there is no problem with bags being damaged by weather conditions.

This method may alternatively be used to cross the plants with perennial teosinte as the female parent. In this embodiment, all the tassels, i.e. male flowers, are removed from the perennial teosinte plant as soon as they emerge and the ears, i.e. female flowers, are covered with pollinating bags. Rather than removing Tripsacum male flowers, the spikes are left in tact and covered with a pollinating bag to collect Tripsacum pollen. The pollen is applied to the diploperennis ears which are then immediately covered with a pollinating bag that is well fastened with staples to ensure it remains sealed until the seed has matured, approximately 45 days after pollination when the seed is harvested.

Next, when (Tripsacum X perennial teosinte) or (perennial teosinte X Tripsacum) starts to flower, the same steps described above are used to cross the hybrid with maize. To cross onto maize, as soon as the maize plants begin to produce ears, before the silks emerge, the ears are covered with an ear shoot bag. Pollen collected from (Tripsacum X perennial teosinte) or (perennial teosinte X Tripsacum) is applied to silks of the maize ears. The ears are then covered again with an ear shoot bag and a large pollinating bag which is wrapped around the culm and secured with a staple. The ears remain covered until they reach maturity, several weeks later when the ears are harvested.

To pollinate the (Tripsacum X perennial teosinte) or (perennial teosinte X Tripsacum) hybrid with maize pollen, the tassel of the maize plant is covered with a large pollinating bag, a day or two before collection. Pistillate flowers of *Tripsacum-diploperennis* hybrid plants frequently have staminate tips above the female flowers as described for Tripsacum. Whenever Tripsacum-perennial teosinte plants are to be pollinated by another plant, all the staminate tips are removed as soon as the ears emerge to prevent possibility of self pollination. The pistillate flowers of the hybrid are covered with an ear shoot bag as soon as they begin to appear on the plant but before the silks emerge. Pollen collected from maize is applied to silks of the hybrid female spikes which are then immediately covered with an ear shoot bag that is stapled closed. The ears remain covered until they reach maturity, approximately 45 days later, and then the seed is harvested.

Plants obtained from all crosses described above are male and female fertile, are cross-fertile with each other, are cross-fertile with maize, and carry novel genetic material, i.e. new alleles from Tripsacum that are not present in maize and the wild Zeas and de novo alleles derived from mutations that arose in the process of intergeneric hybridization, as identified in DNA fingerprints employing 173 different molecular probes distributed throughout the ten linkage groups of maize.

The examples and embodiments described herein are for illustration and modifications or changes that will be suggested to persons skilled in the art are to be included within the spirit and purview of this application and the scope of the appended claims.

TABLE 1

List of Maize Molecular Probes Used to Fingerprint Hybrid and Parent Plants of Tripsacum, *Zea diploperennis*; Tripsacum diploperennis Hybrids, Maize, and Maize-Tripsacum-diploperennis Hybrids.

| Chromosome | 1 | 2 | 3 | 4 | 5 | 6 | 7 | 8 | 9 | 10 | Mitochondrial | Locus unknown |
|---|---|---|---|---|---|---|---|---|---|---|---|---|
| Probe | BNL5.62 | UMC53 | UMC32 | agrr115 | npi409 | UMC85 | asg8 | npi114 | phi10005 | phi20075 | pmt1 | tda16 |
| | npi97 | UMC6 | asg24 | phi20725 | UMC147 | tda50 | O2 | BNL9.11 | UMC113 | BNL3.04 | pmt2 | tda17 |
| | UMC157 | UMC61 | UMC121 | UMC87 | UMC90 | npi373 | BNL15.40 | UMC103 | UMC192 | npi285 | pmt3 | tda48 |
| | UMC76 | UMC34 | BNL8.35 | UMC31 | UMC107 | tda204 | UMC5 | UMC124 | wx | KSU5 | pmt4 | tda53 |
| | UMC11 | UMC135 | UMC50 | UMC55 | UMC27 | UMC59 | UMC116 | tda52 | CSU147 | UMC130 | pmt5 | tda80 |
| | asg45 | UMC131 | UMC42 | BNL5.46 | tda66 | npi393 | tda37 | tda164 | BNL5.10 | UMC64 | pmt6 | tda168 |
| | CSU3 | | npi247 | npi386 | UMC43 | UMC65 | UMC110 | UMC32 | UMC114 | UMC152 | | tda250 |
| | UMC167 | | UMC97 | UMC42 | tda37 | tda51 | tda66 | UMC120 | UMC95 | phi06005 | | |
| | UMC67 | UMC55 | UMC10 | UMC43 | UMC21 | BNL8.32 | UMC89 | CSU61 | tda205 | | | |
| | CSU92 | | UMC102 | UMC40 | UMC46 | BNL14.07 | BNL12.30 | | | | | |
| | asg62 | UMC5 | BNL6.06 | UMC156 | BNL7.17 | UMC132 | UMC80 | UMC30 | BNL7.57 | UMC163 | | |
| | UMC58 | | BNL5.37 | UMC66 | BNL5.71 | asg7 | BNL16.06 | UMC48 | BNL5.09 | UMC44 | | |
| | CSU164 | | npi296 | UMC19 | tda62 | UMC28 | phi20020 | UMC53 | CSU54 | BNL10.13 | | |
| | UMC128 | tda66 | UMC60 | UMC104 | UMC54 | UMC62 | | npi268 | npi97 | npi306 | | |
| | UMC129 | | UMC3 | UMC133 | | UMC134 | | npi414 | UMC94 | | | |
| | UMC107 | UMC4 | npi212 | UMC15 | UMC68 | | | UMC7 | | | | |
| | UMC140 | UMC49 | UMC39 | UMC52 | UMC104 | | | UMC3 | | | | |
| | adh1 | UMC36 | UMC15 | BNL8.23 | php10017 | | | | | | | |
| | UMC161 | | UMC63 | BNL15.07 | | | | | | | | |
| | BNL8.29 | | UMC96 | | | | | | | | | |
| | BNL6.32 | | UMC2 | | | | | | | | | |
| | | | CSU25 | | | | | | | | | |

TABLE 2

Approximate Size of De Novo Restriction Length Fragment Polymorphisms Per Enzyme/Probe Combination.

| Probe | EcoRI | HindIII | BamHI | EcoRV |
|---|---|---|---|---|
| Chromosome 1 | | | | |
| BNL5.62 | 10.3 Kb | — | — | — |
| npi97 | — | 3.9 Kb | — | — |
| UMC157 | 6.5 Kb | 5.5 Kb | 14.0 Kb | — |
| | 3.3 Kb | | 8.6 Kb | |
| | | | 4.5 Kb | |
| UMC11 | — | — | 7.0 Kb | — |
| CSU3 | — | — | 10.0 Kb | — |
| | | | 7.6 Kb | |
| | | | 3.5 Kb | |
| UMC67 | 19.2 Kb | 23.1 Kb | 13.4 Kb | — |
| | | | 11.0 Kb | |
| | | | 1.6 Kb | |
| CSU92 | — | — | 13.3 Kb | — |
| | | | 7.5 Kb | |
| asg62 | — | — | 12.7 Kb | — |
| | | | 9.7 Kb | |
| | | | 6.6 Kb | |
| UMC58 | 15.3 Kb | 3.3 Kb | — | — |
| CSU164 | 9.0 Kb | — | — | — |
| | 7.0 Kb | | | |
| UMC128 | — | 6.0 Kb | — | — |
| UMC107 | 6.3 Kb | 19.2 Kb | — | — |
| | 5.3 Kb | | | |
| UMC140 | 23.0 Kb | 6.5 Kb | — | — |
| | 9.0 Kb | | | |
| | 5.0 Kb | | | |
| adh1 | — | 9.4 Kb | 9.4 Kb | — |
| UMC161 | — | 3.3 Kb | 15.3 Kb | — |
| | | | 8.0 Kb | |
| BNL8.29 | — | 9.3 Kb | — | — |
| | | 8.3 Kb | | |
| Chromosome 2 | | | | |
| UMC53 | 9.4 Kb | — | — | 3.8 Kb |
| | | | | 3.0 Kb |
| UMC6 | 3.8 Kb | 9.4 Kb | 15.3 Kb | — |
| | | | 13.2 Kb | |
| | | | 12.7 Kb | |
| | | | 10.0 Kb | |
| | | | 7.0 Kb | |
| UMC61 | — | 3.4 Kb | — | — |
| | | 2.8 Kb | | |
| UMC34 | 7.5 Kb | 8.8 Kb | 9.4 Kb | — |
| | 5.4 Kb | 6.5 Kb | | |
| | | 5.8 Kb | | |
| UMC135 | — | 11.6 Kb | — | — |
| | | 10.8 Kb | | |
| UMC131 | 10.6 Kb | — | — | — |
| | 5.8 Kb | | | |
| | 4.3 Kb | | | |
| UMC55 | 3.9 Kb | 4.3 Kb | — | — |
| UMC5 | 5.4 Kb | 6.5 Kb | — | — |
| UMC49 | — | — | 8.2 Kb | — |
| | | | 6.0 Kb | |
| | | | 4.2 Kb | |
| | | | 3.2 Kb | |
| UMC36 | — | — | 4.2 Kb | — |
| Chromosome 3 | | | | |
| UMC32 | 5.3 Kb | 6.7 Kb | — | — |
| asg24 | — | 7.2 Kb | — | — |
| | | 6.4 Kb | | |
| UMC121 | 3.7 Kb | — | — | — |
| | 3.2 Kb | | | |

TABLE 2-continued

Approximate Size of De Novo Restriction Length Fragment Polymorphisms Per Enzyme/Probe Combination.

| Probe | EcoRI | HindIII | BamHI | EcoRV |
|---|---|---|---|---|
| BNL8.35 | — | 9.9 Kb | — | — |
|  |  | 8.7 Kb |  |  |
| UMC50 | — | — | 6.8 Kb | — |
|  |  |  | 3.8 Kb |  |
| UMC42 | — | 1.4 Kb | — | — |
|  |  | 8.9 Kb |  |  |
|  |  | 3.7 Kb |  |  |
|  |  | 3.0 Kb |  |  |
| npi247 | 8.0 Kb | 3.0 Kb | — | — |
| UMC10 | 6.5 Kb | 5.9 Kb | — | — |
|  | 5.5 Kb | 3.0 Kb |  |  |
| UMC102 | 2.7 Kb | — | — | — |
| BNL6.06 | 6.8 Kb | — | — | — |
| BNL5.37 | — | 10.3 Kb | — | — |
|  |  | 5.8 Kb |  |  |
|  |  | 3.5 Kb |  |  |
| npi296 | 7.9 Kb | — | — | — |
| UMC3 | 2.5 Kb | — | — | — |
|  | 2.0 Kb |  |  |  |
| npi212 | — | 4.3 Kb | 5.4 Kb | — |
| UMC39 | 12.2 Kb | — | — | — |
|  | 9.2 Kb |  |  |  |
|  | 7.8 Kb |  |  |  |
|  | 7.1 Kb |  |  |  |
| UMC63 | — | 9.5 Kb | — | — |
|  |  | 4.3 Kb |  |  |
| UMC96 | — | 11.8 Kb | 7.5 Kb | — |
|  |  | 6.4 Kb |  |  |
|  |  | 5.5 Kb |  |  |
| UMC2 | 11.8 Kb | — | — | — |
|  | 10.4 Kb |  |  |  |
|  | 8.0 Kb |  |  |  |
| CSU25 | — | 4.6 Kb | — | — |
|  |  | 4.3 Kb |  |  |

Chromosome 4

| Probe | EcoRI | HindIII | BamHI | EcoRV |
|---|---|---|---|---|
| agrr115 | 8.0 Kb | 19.2 Kb | 5.4 Kb | — |
|  | 5.4 Kb |  | 3.5 Kb |  |
| phi20725 | 10.3 Kb | 1.5 Kb | — | — |
|  | 7.2 Kb |  |  |  |
| UMC31 | 5.8 Kb | — | 6.5 Kb | — |
| UMC55 | 3.9 Kb | 4.3 Kb | — | — |
| BNL5.46 | — | 13.7 Kb | — | — |
|  |  | 10.5 Kb |  |  |
|  |  | 9.7 Kb |  |  |
|  |  | 5.1 Kb |  |  |
| npi386 | — | 9.3 Kb | — | — |
|  |  | 8.2 Kb |  |  |
| UMC42 | — | 19.2 Kb | — | — |
|  |  | 10.3 Kb |  |  |
|  |  | 8.9 Kb |  |  |
|  |  | 3.7 Kb |  |  |
|  |  | 3.0 Kb |  |  |
| tda62 | — | — | 5.5 Kb | — |
| BNL5.71 | — | — | — | 11.3 Kb |
|  |  |  |  | 6.8 Kb |
|  |  |  |  | 5.7 Kb |
| UMC156 | — | 3.0 Kb | — | — |
| UMC66 | 10.5 Kb | — | 3.7 Kb | — |
| UMC19 | — | — | 12.3 Kb | — |
| UMC104 | — | 12.4 Kb | — | — |
|  |  | 11.6 Kb |  |  |
|  |  | 7.5 Kb |  |  |
| UMC133 | — | 10.6 Kb | — | — |
|  |  | 9.9 Kb |  |  |
|  |  | 9.2 Kb |  |  |
|  |  | 7.7 Kb |  |  |
| UMC52 | — | — | 8.7 Kb | — |
|  |  |  | 6.9 Kb |  |
|  |  |  | 3.8 Kb |  |
|  |  |  | 3.0 Kb |  |
|  |  |  | 2.0 Kb |  |
| BNL15.07 | — | 2.9 Kb | — | — |
|  |  | 2.7 Kb |  |  |

Chromosome 5

| Probe | EcoRI | HindIII | BamHI | EcoRV |
|---|---|---|---|---|
| npi409 | 9.4 Kb | 10.4 Kb | 19.2 Kb | — |
|  |  | 9.0 Kb |  |  |
|  |  | 3.9 Kb |  |  |
|  |  | 3.0 Kb |  |  |
| UMC147 | — | 16.3 Kb | — | — |
|  |  | 3.8 Kb |  |  |
|  |  | 2.4 Kb |  |  |
| UMC90 | — | 2.8 Kb | 9.0 Kb | — |
|  |  | 2.5 Kb |  |  |
|  |  | 1.6 |  |  |
| UMC107 | 6.3 Kb | — | — | — |
| UMC27 | — | 4.5 Kb | 6.5 Kb | — |
| tda37 | — | — | 8.2 Kb | — |
|  |  |  | 6.5 Kb |  |
| UMC43 | — | — | 9.7 Kb | — |
|  |  |  | 7.3 Kb |  |
|  |  |  | 9.7 Kb |  |
| UMC40 | — | — | 7.2 Kb | — |
|  |  |  | 4.3 Kb |  |
|  |  |  | 4.0 Kb |  |
| BNL7.71 | — | 10.6 Kb | — | — |
| BNL5.71 | — | — | — | 11.3 Kb |
|  |  |  |  | 6.8 Kb |
|  |  |  |  | 5.7 Kb |
| tda62 | — | — | 5.5 Kb | — |
| UMC68 | — | 6.0 Kb | — | — |
| UMC104 | — | 12.4 Kb | 9.4 Kb | — |
|  |  | 11.6 Kb |  |  |
|  |  | 7.5 Kb |  |  |
| phi10017 | — | — | — | 15.1 Kb |
|  |  |  |  | 9.5 Kb |

Chromosome 6

| Probe | EcoRI | HindIII | BamHI | EcoRV |
|---|---|---|---|---|
| tda50 | — | — | 8.5 Kb | — |
| npi373 | — | 6.5 Kb | — | — |
|  |  | 5.6 Kb |  |  |
|  |  | 3.0 Kb |  |  |
| tda204 | — | — | — | 4.0 Kb |
| npi393 | 12.1 Kb | — | — | — |
|  | 8.5 Kb |  |  |  |
|  | 5.6 Kb |  |  |  |
| UMC65 | — | 2.9 Kb | — | — |
| UMC21 | 5.7 Kb | — | — | — |
| UMC46 | 6.5 Kb | — | — | — |
|  | 5.6 Kb |  |  |  |
| asg7 | — | 6.3 Kb | — | — |
| UMC28 | — | 15.8 Kb | 7.6 Kb | — |
|  |  | 11.9 Kb | 6.6 Kb |  |
| UMC134 | 15.3 Kb | 7.5 Kb | 4.7 Kb | — |

Chromosome 7

| Probe | EcoRI | HindIII | BamHI | EcoRV |
|---|---|---|---|---|
| asg8 | — | 10.8 Kb | — | — |
|  |  | 8.4 Kb |  |  |
| O$_2$ | 9.4 Kb | — | — | — |
| BNL15.40 | — | 5.8 Kb | — | — |
| UMC116 | 9.5 Kb | 15.3 Kb | — | — |
| UMC110 | — | — | 10.6 Kb | — |
|  |  |  | 4.9 Kb |  |
| BNL8.32 | — | 8.9 Kb | — | — |
|  |  | 7.4 Kb |  |  |
|  |  | 7.1 Kb |  |  |
| BNL14.07 | 6.4 Kb | — | — | — |
| UMC80 | — | — | 2.4 Kb | — |
| BNL16.06 | 6.8 Kb | — | — | — |
| phi20020 | — | 7.8 Kb | — | — |
|  |  | 6.6 KB |  |  |

TABLE 2-continued

Approximate Size of De Novo Restriction Length Fragment Polymorphisms Per Enzyme/Probe Combination.

| Probe | EcoRI | HindIII | BamHI | EcoRV |
|---|---|---|---|---|
| Chromosome 8 | | | | |
| npi114 | — | 10.0 Kb | — | — |
| | | 8.8 Kb | | |
| | | 6.3 KB | | |
| BNL9.11 | — | 3.4 Kb | — | — |
| UMC103 | — | 6.9 Kb | — | — |
| | | 5.7 Kb | | |
| UMC124 | — | 8.0 Kb | 21.0 Kb | — |
| | | 7.0 Kb | 19.0 Kb | |
| | | | 6.6 Kb | |
| | | | 2.6 Kb | |
| | | | 1.6 Kb | |
| UMC120 | — | 8.0 Kb | 23.1 Kb | — |
| | | 3.2 Kb | | |
| | | 2.3 Kb | | |
| | | 1.4 Kb | | |
| UMC89 | 7.3 Kb | 7.3 Kb | 9.5 Kb | — |
| | | | 6.0 Kb | |
| | | | 5.2 Kb | |
| | | | 4.5 Kb | |
| BNL12.30 | 3.5 Kb | — | — | — |
| UMC48 | — | 4.7 Kb | — | — |
| | | 3.5 Kb | | |
| | | 2.2 Kb | | |
| UMC53 | 3.8 Kb | — | — | — |
| | 3.0 Kb | | | |
| npi268 | — | — | 6.4 Kb | — |
| UMC3 | 2.5 Kb | — | — | — |
| | 2.0 Kb | | | |
| Chromosome 9 | | | | |
| phi10005 | 15.0 Kb | — | — | — |
| UMC113 | 5.9 Kb | — | 12.8 Kb | — |
| | 5.4 Kb | | 11.8 Kb | |
| | | | 10.5 Kb | |
| UMC192 | — | 11.4 Kb | — | — |
| | | 6.4 Kb | | |
| wx (waxy) | — | 21.0 Kb | — | — |
| CSU147 | — | 5.9 Kb | — | — |
| BNL5.10 | — | 6.1 Kb | — | — |
| | | 4.4 Kb | | |
| UMC114 | — | — | 15.0 Kb | — |
| | | | 12.6 Kb | |
| | | | 11.5 Kb | |
| | | | 10.0 Kb | |
| | | | 8.8 Kb | |
| | | | 7.5 Kb | |
| | | | 6.5 Kb | |
| UMC95 | 13.3 Kb | 7.7 Kb | 15.0 Kb | — |
| | 5.6 Kb | 4.8 Kb | 9.0 Kb | |
| | | 4.1 Kb | | |
| CSU61 | 8.1 Kb | — | — | — |
| | 4.8 Kb | | | |
| bnl7.57 | 1.0 Kb | — | 11.6 Kb | — |
| | | | 5.9 Kb | |
| | | | 5.5 Kb | |
| | | | 1.3 Kb | |
| CSU54 | 14.7 Kb | — | — | — |
| | 12.6 Kb | | | |
| Chromosome 10 | | | | |
| phi20075 | 7.1 Kb | — | — | — |
| npi285 | 15.3 Kb | — | — | — |
| | 12.4 Kb | | | |
| | 9.4 Kb | | | |
| | 6.0 Kb | | | |
| KSU5 | 9.8 Kb | — | — | — |
| | 7.6 Kb | | | |
| | 6.1 Kb | | | |
| | 3.8 Kb | | | |
| | 3.5 Kb | | | |
| UMC130 | 13.5 Kb | 4.8 Kb | 3.2 Kb | — |
| | 7.0 Kb | 3.2 Kb | | |
| UMC152 | — | 12.4 Kb | — | — |
| | | 7.1 Kb | | |
| | | 5.6 Kb | | |
| UMC64 | — | 3.3 Kb | — | — |
| phi06005 | 12.8 Kb | — | — | — |
| UMC163 | — | 12.0 Kb | — | — |
| | | 7.0 Kb | | |
| | | 4.8 Kb | | |
| UMC44 | — | 9.8 Kb | — | — |
| | | 8.7 Kb | | |
| | | 7.2 Kb | | |
| | | 5.5 Kb | | |
| | | 4.0 Kb | | |
| BNL10.13 | — | 10.8 Kb | — | — |
| npi306 | — | 7.0 Kb | — | — |
| Mitochondria | | | | |
| pmt1 | — | 2.3 Kb | — | — |
| pmt2 | — | 8.0 Kb | — | — |
| | | 4.2 Kb | | |
| | | 2.8 Kb | | |
| | | 2.1 Kb | | |
| pmt5 | — | 12.3 Kb | — | — |
| | | 8.1 Kb | | |
| | | 3.2 Kb | | |
| | | 2.5 Kb | | |
| Map Location Unknown | | | | |
| tda16 | — | 4.3 Kb | — | — |
| tda17 | — | 7.0 Kb | — | — |
| tda37 | — | — | 8.2 Kb | — |
| | | | 6.5 Kb | |
| tda48 | — | 8.2 Kb | — | — |
| tda53 | — | 3.8 Kb | — | — |
| | | 2.2 Kb | | |

TABLE 3

Approximate Size of New Tripsacum Restriction Length Fragment Polymorphisms Per Enzyme/Probe Combination Not Present in Maize or the Wild Zeas.

| Probe | EcoRI | HindIII | BamHI | EcoRV |
|---|---|---|---|---|
| Chromosome 2 | | | | |
| UMC53 | — | — | — | 8.4 Kb |
| Chromosome 3 | | | | |
| UMC50 | — | — | 7.8 Kb | — |
| | | | 5.8 Kb | |
| UMC42 | — | 7.6 Kb | — | — |
| Chromosome 4 | | | | |
| phi20725 | 9.7 Kb | — | — | — |
| npi386 | — | 12.6 Kb | — | — |
| UMC42 | — | 7.6 Kb | — | — |
| tda62 | — | — | 4.8 Kb | — |
| Chromosome 5 | | | | |
| UMC90 | — | 7.8 Kb | — | — |
| UMC27 | — | 8.3 Kb | — | — |

TABLE 3-continued

Approximate Size of New Tripsacum Restriction Length Fragment Polymorphisms Per Enzyme/Probe Combination Not Present in Maize or the Wild Zeas.

| Probe | Restriction Enzyme | | | |
|---|---|---|---|---|
| | EcoRI | HindIII | BamHI | EcoRV |
| Chromosome 6 | | | | |
| tda50 | — | — | 6.8 Kb | — |
| npi393 | 7.0 Kb | — | — | — |
| UMC28 | — | — | 10.0 Kb | — |
| Chromosome 7 | | | | |
| asg8 | — | 8.7 Kb | — | — |
| UMC110 | — | — | 3.9 Kb | — |
| UMC80 | — | 10.6 Kb | — | — |
| | | 8.2 Kb | | |
| BNL16.06 | — | 1.9 Kb | — | — |
| Chromosome 8 | | | | |
| UMC48 | — | 6.2 Kb | — | — |
| UMC53 | — | — | — | 8.4 Kb |
| Chromosome 10 | | | | |
| UMC163 | — | 2.6 Kb | — | — |
| Mitochondria | | | | |
| pmt5 | — | 3.6 Kb | — | — |
| Map Location Unknown | | | | |
| tda168 | 3.6 Kb | — | — | — |

TABLE 4

De Novo Alleles in *Tripsacum-diploperennis* Hybrids and Maize X *Tripsacum-diploperennis*

| | *Tripsacum-diploperennis* Hybrids | | | | Maize X *Tripsacum-diploperennis* | | | | | | | |
|---|---|---|---|---|---|---|---|---|---|---|---|---|
| Probe/Enzyme | Sun Dance | 20A | Tripsacorn | Sun Star | 64SS | 64TC | 2019 | 3024 | 3028 | 3125 | 4126 | TC64 |
| Chromosome 1 | | | | | | | | | | | | |
| BNL5.62-ERI | 10.3 kb | | | | | | 10.3 kb | 10.3 kb | 10.3 kb | | | |
| npi-97-H | 3.9 kb | | 3.9 kb | | | | 3.9 kb | 3.9 kb | 3.9 kb | 3.9 kb | | |
| UMC157-ERI | 6.5 kb | | 6.5 kb | | | 6.5 kb | | | | | | |
| UMC157-ERI | 3.3 kb | | 3.3 kb | | | 3.3 kb | | | | | | |
| UMC157-H | 5.5 kb | | 5.5 kb | | | 5.5 kb | | | | | | |
| UMC157-B | 14.0 kb | 14.0 kb | 14.0 kb | 14.0 kb | 14.0 kb | 14.0 kb | | | 14.0 kb | | | |
| UMC157-B | | 8.6 kb | | 8.6 kb | | | | | 8.6 kb | | | |
| UMC157-B | | | 4.5 kb | 4.5 kb | | | 4.5 kb | | | | | 4.5 kb |
| UMC11-B | 7.0 kb | 7.0 kb | 7.0 kb | 7.0 kb | | | 7.0 kb | 7.0 kb | | 7.0 kb | | 7.0 kb |
| CSU3-B | | | 10.0 kb | 10.0 kb | | | 10.0 kb | 10.0 kb | | | 10.0 kb | 10.0 kb |
| CSU3-B | | | 7.6 kb | 7.6 kb | | | 7.6 kb | 7.6 kb | | | 7.6 kb | 7.6 kb |
| CSU3-B | 3.5 kb | | 3.5 kb | | | | | | | 3.5 kb | | 3.5 kb |
| UMC67-ERI | | | | 19.2 kb | | | | | | | | |
| UMC67-H | | | | 23.1 kb | | | | | | | | |
| UMC67-B | 13.4 kb | | | | | | | | | | | |
| UMC67-B | 11.0 kb | 11.0 kb | 11.0 kb | 11.0 kb | | | 11.0 kb | 11.0 kb | 11.0 kb | 11.0 kb | 11.0 kb | 11.0 kb |
| UMC67-B | | | | 1.6 kb | | | | | | | | |
| CSU92-B | 13.3 kb | | 13.3 kb | 13.3 kb | | | 13.3 kb | 13.3 kb | | | | 13.3 kb |
| CSU92-B | 7.5 kb | 7.5 kb | | | | | | | | | | |
| asg62-B | 12.7 kb | | 12.7 kb | 12.7 kb | | | | | | | | |
| asg62-B | | 9.7 kb | 9.7 kb | 9.7 kb | | | 9.7 kb | 9.7 kb | 9.7 kb | | 9.7 kb | |
| asg62-B | 6.6 kb | | 6.6 kb | | | | | | | | | |
| UMC58-ERI | 15.3 kb | | 15.3 kb | 15.3 kb | 15.3 kb | 15.3 kb | | | | | | |
| UMC58-H | 3.3 kb | | 3.3 kb | 3.3 kb | 3.3 kb | 3.3 kb | | | | | | |
| CSU164-ERI | 9.0 kb | | 9.0 kb | | | | 9.0 kb | 9.0 kb | | | 9.0 kb | |
| CSU164-ERI | | 7.0 kb | | | | | | | | | | |
| UMC128-H | | | 6.0 kb | 6.0 kb | | | 6.0 kb | 6.0 kb | | | 6.0 kb | 6.0 kb |
| UMC107-ERI | | | 6.3 kb | 6.3 kb | 6.3 kb | | | | | | | |
| UMC107-ERI | 5.3 kb | | 5.3 kb | | | 5.3 kb | | | | | | |
| UMC107-H | 19.2 kb | | 19.2 kb | | | | | | | | | |
| UMC140-ERI | 23.0 kb | | | | | | | | | | | |
| UMC140-ERI | 9.0 kb | | 9.0 kb | | | | | | | | | |
| UMC140-ERI | 5.0 kb | | 5.0 kb | 5.0 kb | | | 5.0 kb | 5.0 kb | 5.0 kb | | | 5.0 kb |
| UMC140-H | 6.5 kb | | 6.5 kb | | | | | | | | | |
| adh1-H | 9.4 kb | | 9.4 kb | 9.4 kb | | | | | | | | |
| adh1-B | 9.4 kb | | 9.4 kb | 9.4 kb | 9.4 kb | 9.4 kb | | | | | | |
| UMC161-H | 3.3 kb | | 3.3 kb | 3.3 kb | 3.3 kb | 3.3 kb | | | | | | |

TABLE 4-continued

De Novo Alleles in *Tripsacum*-*diploperennis* Hybrids and Maize X *Tripsacum* - *diploperennis*

| | *Tripsacum*-*diploperennis* Hybrids | | | | Maize X *Tripsacum* - *diploperennis* | | | | | | | |
|---|---|---|---|---|---|---|---|---|---|---|---|---|
| Probe/Enzyme | Sun Dance | 20A | Tripsacorn | Sun Star | 64SS | 64TC | 2019 | 3024 | 3028 | 3125 | 4126 | TC64 |
| UMC161-B | 15.3 kb | | | | | | | | | | | |
| UMC161-B | | | 8.0 kb | 8.0 kb | | | | | | | | |
| BNL8.29-H | | | 9.3 kb | | | | | | | | 9.3 kb | |
| BNL8.29-H | 8.3 kb | 8.3 kb | 8.3 kb | 8.3 kb | | | | | | | | 8.3 kb |
| Chromosome 2 | | | | | | | | | | | | |
| UMC53-ERI | 9.4 kb | | 9.4 kb | 9.4 kb | 9.4 kb | | | | | | | |
| UMC53-ERV | | 3.8 kb | 3.8 kb | 3.8 kb | | | 3.8 kb | 3.8 kb | 3.8 kb | | | 3.8 kb |
| UC53-ERV | 3.0 kb | | | | | | | | | | | |
| UMC6-ERI | | | 3.8 kb | | | | | | | | | |
| UMC6-H | | | 9.4 kb | 9.4 kb | 9.4 kb | | | | | | | |
| UMC6-B | | | 15.3 kb | | | | | | | | | |
| UMC6-B | 13.2 kb | 13.2 kb | | | | | | | | | | |
| UMC6-B | | | | 12.7 kb | | | | | | | | |
| UMC6-B | | 10.0 kb | | | | | | | | | | |
| UMC6-B | 7.0 kb | 7.0 kb | | | | | | | | | | |
| UMC61-H | | | 3.4 kb | 3.4 kb | | | | | | | | |
| UMC61-H | 2.8 kb | | 2.8 kb | 2.8 kb | | | 2.8 kb | 2.8 kb | 2.8 kb | 2.8 kb | 2.8 kb | 2.8 kb |
| UMC34-ERI | 7.5 kb | | | | | | | | | | | |
| UMC34-ERI | 5.4 kb | | 5.4 kb | 5.4 kb | 5.4 kb | | | | | | | |
| UMC34-H | 8.8 kb | | 8.8 kb | 8.8 kb | 8.8 kb | | | | | | | |
| UMC34-H | 6.5 kb | | 6.5 kb | | | | | | | | | |
| UMC34-H | 5.8 kb | 5.8 kb | | | | | 5.8 kb | 5.8 kb | | 5.8 kb | 5.8 kb | 5.8 kb |
| UMC34-B | | | 9.4 kb | 9.4 kb | 9.4 kb | | | | | | | |
| UMC135-H | | 11.6 kb | | | | | | | | | | |
| UMC135-H | | | 10.8 kb | | | | 10.8 kb | 10.8 kb | | 10.8 kb | | |
| UMC131-ERI | | | 10.6 kb | | | | | | | | | |
| UMC131-ERI | 5.8 kb | | | | | | | | | | | |
| UMC131-ERI | 4.3 kb | 4.3 kb | 4.3 kb | 4.3 kb | 4.3 kb | 4.3 kb | 4.3 kb | 4.3 kb | 4.3 kb | | | |
| UMC55-ERI | 3.9 kb | 3.9 kb | 3.9 kb | | | | 3.9 kb | 3.9 kb | | 3.9 kb | 3.9 kb | 3.9 kb |
| UMC55-H | 4.3 kb | | 4.3 kb | | | | | | | | | |
| UMC5-ERI | 5.4 kb | | 5.4 kb | 5.4 kb | 5.4 kb | | | | | | | |
| UMC5-H | | | 6.5 kb | 6.5 kb | 6.5 kb | | | | | | | |
| UMC49-B | | 8.2 kb | 8.2 kb | | | | | | | | | |
| UMC49-B | | 6.0 kb | 6.0 kb | 6.0 kb | | | | | | | | |
| UMC49-B | | | 4.2 kb | 4.2 kb | | | | | 4.2 kb | | 4.2 kb | 4.2 kb |
| UMC49-B | 3.2 kb | | | | | | | | | | | |
| UMC36-B | 4.2 kb | | | | | | | | | | | |
| Chromosome 3 | | | | | | | | | | | | |
| UMC32-ERI | 5.3 kb | | 5.3 kb | 5.3 kb | 5.3 kb | 5.3 kb | 6.7 kb | 6.7 kb | | 6.7 kb | 6.7 kb | 6.7 kb |
| UMC32-H | 6.7 kb | | 6.7 kb | 6.7 kb | | | | | | | | |
| asg24-H | 7.2 kb | 7.2 kb | 7.2 kb | 7.2 kb | | | | | 7.2 kb | 7.2 kb | 7.2 kb | 7.2 kb |
| asg24-H | 6.4 kb | | 6.4 kb | 6.4 kb | | | | | | 6.4 kb | | 6.4 kb |
| UMC121-ERI | 3.7 kb | 3.7 kb | 3.7 kb | 3.7 kb | | | | 3.7 kb | 3.7 kb | | | 3.7 kb |
| UMC121-ERI | 3.2 kb | 3.2 kb | | 3.2 kb | | | | | | | | |
| BNL8.35-H | | | 9.9 kb | | | | | | | | | |
| BNL8.35-H | | 8.7 kb | | | | | | | | | | |
| UMC50-B | 6.8 kb | | | | | | | | | | | |
| UMC50-B | | | 3.8 kb | | | | | | 3.8 kb | 3.8 kb | 3.8 kb | |
| UMC42-H | 10.4 kb | 10.4 kb | 10.4 kb | 10.4 kb | | | 10.4 kb | 10.4 kb | 10.4 kb | 10.4 kb | 10.4 kb | 10.4 kb |
| UM042-H | | 8.9 kb | | 8.9 kb | | | | | 8.9 kb | | | |
| UM042-H | 3.7 kb | | 3.7 kb | | | | 3.7 kb | 3.7 kb | 3.7 kb | 3.7 kb | 3.7 kb | 3.7 kb |
| UM042-H | 3.0 kb | | | | | | | | | | | |
| npi247-ERI | 8.0 kb | | 8.0 kb | 8.0 kb | 8.0 kb | | | | | | | |
| npi247-H | | | 3.0 kb | 3.0 kb | 3.0 kb | | | | | | | |
| UMC10-ERI | | | 6.5 kb | 6.5 kb | 6.5 kb | | | | | | | |
| UMC10-ERI | | | 5.5 kb | 5.5 kb | 5.5 kb | | | | | | | |
| UMC10-H | 5.9 kb | | | 5.9 kb | | | | | | | | |
| UMC10-H | 3.0 kb | | | 3.0 kb | | | | | | | | |
| UMC102-ERI | | 2.7 kb | | 2.7 kb | | | | | | 2.7 kb | | |
| BNL6.06-ERI | 6.8 kb | 6.8 kb | 6.8 kb | 6.8 kb | | | | 6.8 kb | 6.8 kb | | | 6.8 kb |
| BNL5.37-H | | | 10.3 kb | 10.3 kb | | | 10.3 kb | 10.3 kb | 10.3 kb | 10.3 kb | 10.3 kb | 10.3 kb |
| BNL5.37-H | 5.8 kb | 5.8 kb | 5.8 kb | 5.8 kb | | | | | | 5.8 kb | | 5.8 kb |
| BNL5.37-H | 3.5 kb | 3.5 kb | 3.5 kb | 3.5 kb | | | 3.5 kb | 3.5 kb | 3.5 kb | 3.5 kb | 3.5 kb | 3.5 kb |
| npi296-ERI | 7.9 kb | | 7.9 kb | 7.9 kb | 7.9 kb | 7.9 kb | | | | | | |
| UMC3-ERI | 2.5 kb | | 2.5 kb | 2.5 kb | | | 2.5 kb | 2.5 kb | | 2.5 kb | 2.5 kb | 2.5 kb |
| UMC3-ERI | 2.0 kb | 2.0 kb | | | | | | | | | | |
| npi212-H | | | 4.3 kb | 4.3 kb | | | | | | | | |
| npi212-B | | | 5.4 kb | 5.4 kb | | | | | | | | |
| UMC39-ERI | 12.2 kb | 12.2 kb | | | | | | | | 12.2 kb | | |
| UMC39-ERI | | 9.2 kb | | 9.2 kb | | | | | | 9.2 kb | | |
| UMC39-ERI | 7.8 kb | 7.8 kb | | 7.8 kb | | | | | | | | |

TABLE 4-continued

De Novo Alleles in *Tripsacum*-*diploperennis* Hybrids and Maize X *Tripsacum*-*diploperennis*

| | *Tripsacum*-*diploperennis* Hybrids | | | | Maize X *Tripsacum*-*diploperennis* | | | | | | | |
|---|---|---|---|---|---|---|---|---|---|---|---|---|
| Probe/Enzyme | Sun Dance | 20A | Tripsacorn | Sun Star | 64SS | 64TC | 2019 | 3024 | 3028 | 3125 | 4126 | TC64 |
| UMC39-ERI | 7.1 kb | | 7.1 kb | 7.1 kb | | | | 7.1 kb | | 7.1 kb | 7.1 kb | 7.1 kb |
| UMC63-H | | | | 9.5 kb | | | 9.5 kb | | 9.5 kb | 9.5 kb | 9.5 kb | 9.5 kb |
| UMC63-H | 4.3 kb | 4.3 kb | | 4.3 kb | | | | | 4.3 kb | | | |
| UMC96-H | | | 11.8 kb | 11.8 kb | | | 11.8 kb | 11.8 kb | | | | |
| UMC96-H | | | | 6.4 kb | | | | | 6.4 kb | | | |
| UMC96-H | 5.5 kb | | 5.5 kb | 5.5 kb | | | | | | | | |
| UMC96-B | 7.5 kb | | | | | | | | | | | |
| UMC2-ERI | 11.8 kb | | 11.8 kb | | | | | | | 11.8 kb | 11.8 kb | |
| UMC2-ERI | | | | 10.4 kb | | | | | | | | |
| UMC2-ERI | | 8.0 kb | | 8.0 kb | | | | | 8.0 kb | | | |
| CSU25-H | 4.6 kb | | | | | | | | | 4.6 kb | 4.6 kb | 4.6 kb |
| CSU25-H | 4.2 kb | 4.2 kb | | 4.2 kb | | | | | 4.2 kb | | | |
| Chromosome 4 | | | | | | | | | | | | |
| agrr115-ERI | | | 8.0 kb | 8.0 kb | 8.0 kb | 8.0 kb | | | | | | |
| agrr115-ERI | 5.4 kb | | 5.4 kb | | 5.4 kb | 5.4 kb | | | | | | |
| agrr115-H | | | 19.2 kb | 19.2 kb | 19.2 kb | | | | | | | |
| agrr115-B | | | 5.4 kb | 5.4 kb | 5.4 kb | 5.4 kb | | | | | | |
| agrr115-B | | | 3.5 kb | 3.5 kb | 3.5 kb | 3.5 kb | | | | | | |
| phi20725-ERI | | | 10.3 kb | 10.3 kb | | | | | | | | 10.3 kb |
| phi20725-ERI | | 7.2 kb | | 7.2 kb | | | | 7.2 kb | | | | |
| phi20725-H | 1.5 kb | | | | | | | | | | | |
| UMC31-ERI | | | 5.8 kb | 5.8 kb | 5.8 kb | | | | | | | |
| UMC55-ERI | 3.9 kb | 3.9 kb | 3.9 kb | | | | 3.9 kb | 3.9 kb | | 3.9 kb | 3.9 kb | 3.9 kb |
| UMC55-H | 4.3 kb | | 4.3 kb | | | | | | | | | |
| BNL5.46-B | 13.7 kb | | | | | | | | | | | |
| BNL5.46-B | | 10.5 kb | | 10.5 kb | | | | | | | | |
| BNL5.46-B | 9.7 kb | | 9.7 kb | 9.7 kb | | | 9.7 kb | 9.7 kb | 9.7 kb | 9.7 kb | 9.7 kb | 9.7 kb |
| BNL5.46-B | | | 5.1 kb | | | | | | 5.1 kb | | | |
| npi386-H | 9.3 kb | 9.3 kb | | | | | | | | | | |
| npi386-H | 8.2 kb | | 8.2 kb | | | | | | | 8.2 kb | | |
| UMC42-H | 19.2 kb | | 19.2 kb | 19.2 kb | 19.2 kb | 19.2 kb | | | | | | |
| UMC42-H | 10.3 kb | 10.3 kb | 10.3 kb | 10.3 kb | | | 10.3 kb | 10.3 kb | 10.3 kb | 10.3 kb | 10.3 kb | 10.3 kb |
| UMC42-H | | 8.9 kb | | 8.9 kb | | | | | 8.9 kb | | | |
| UMC42-H | 3.7 kb | | 3.7 kb | | | | 3.7 kb | 3.7 kb | 3.7 kb | 3.7 kb | 3.7 kb | 3.7 kb |
| UMC42-H | 3.0 kb | | | | | | | | | | | |
| tda62-B | 5.5 kb | 5.5 kb | 5.5 kb | | | | | | | 5.5 kb | | |
| BNL5.71-ERV | 11.3 kb | 11.3 kb | 11.3 kb | 11.3 kb | | | | | | | | 11.3 kb |
| BNL5.71-ERV | | 6.8 kb | | 6.8 kb | | | | | 6.8 kb | | | |
| BNL5.71-ERV | 5.7 kb | | 5.7 kb | | | | 5.7 kb | 5.7 kb | | 5.7 kb | 5.7 kb | 5.7 kb |
| UMC156-H | 3.0 kb | | 3.0 kb | 3.0 kb | 3.0 kb | | | | | | | |
| UMC66-ERI | | | 10.5 kb | 10.5 kb | | | | | | | | |
| UMC66-B | 3.7 kb | 3.7 kb | 3.7 kb | 3.7 kb | | | 3.7 kb | 3.7 kb | 3.7 kb | 3.7 kb | 3.7 kb | 3.7 kb |
| UMC19-B | 12.3 kb | 12.3 kb | 12.3 kb | 12.3 kb | | | 12.3 kb | 12.3 kb | 12.3 kb | | 12.3 kb | 12.3 kb |
| UMC104-H | | | | 12.4 kb | | | | | | | | |
| UMC104-H | 11.6 kb | | 11.6 kb | | | | | | | | | |
| UMC104-H | | 7.5 kb | | | | | | | | | | |
| UMC133-H | 10.6 kb | 10.6 kb | 10.6 kb | | | | | | | | | |
| UMC133-H | | | | 9.9 kb | | | | | | | | |
| UMC133-H | | | 9.2 kb | | | | | | 9.2 kb | 9.2 kb | 9.2 kb | 9.2 kb |
| UMC133-H | | | | 7.7 kb | | | | | | | | |
| UMC52-B | | | 8.7 kb | 8.7 kb | | | 8.7 kb | 8.7 kb | | 8.7 kb | 8.7 kb | 8.7 kb |
| UMC52-B | 6.9 kb | | | | | | | | | | | |
| UMC52-B | 3.8 kb | | 3.8 kb | | | 3.8 kb | | | | | | |
| UMC52-B | 3.0 kb | | | | | | | | | | | |
| UMC52-B | | | 2.0 kb | 2.0 kb | 2.0 kb | | | | | | | |
| BNL15.07-H | 2.9 kb | | | | | | | | | | | |
| BNL15.07-H | | | | 2.7 kb | | | | | | | | |
| Chromosome 5 | | | | | | | | | | | | |
| npi409-ERI | 9.4 kb | | 9.4 kb | | | | | | | | | |
| npi409-ERI | | | 10.4 kb | | | | | | | | | |
| npi409-H | | | 9.0 kb | 9.0 kb | 9.0 kb | | | | | | | |
| npi409-H | 3.9 kb | 3.9 kb | 3.9 kb | 3.9 kb | | 3.9 kb | 3.9 kb | 3.9 kb | 3.9 kb | 3.9 kb | 3.9 kb | 3.9 kb |
| npi409-H | 3.0 kb | | 3.0 kb | 3.0 kb | 3.0 kb | 3.0 kb | | | | | | |
| npi409-B | | | 19.2 kb | 19.2 kb | 19.2 kb | | | | | | | |
| UMC147-H | | 16.3 kb | | 16.3 kb | | | 16.3 kb | 16.3 kb | | | | |
| UMC147-H | 3.8 kb | | | | | | | | | | | |
| UMC147-H | 2.4 kb | | 2.4 kb | | | | 2.4 kb | 2.4 kb | | 2.4 kb | | |
| UMC90-H | 2.8 kb | | | | | | | | | | | |
| UMC90-H | 2.5 kb | | | 2.5 kb | | | | | | | | |
| UMC90-H | 1.6 kb | | | | | | | | | | | |
| UMC90-B | | | 9.0 kb | 9.0 kb | 9.0 kb | | | | | | | |

TABLE 4-continued

De Novo Alleles in *Tripsacum -diploperennis* Hybrids and Maize X *Tripsacum - diploperennis*

| | *Tripsacum -diploperennis* Hybrids | | | | Maize X *Tripsacum - diploperennis* | | | | | | | |
|---|---|---|---|---|---|---|---|---|---|---|---|---|
| Probe/Enzyme | Sun Dance | 20A | Tripsacorn | Sun Star | 64SS | 64TC | 2019 | 3024 | 3028 | 3125 | 4126 | TC64 |
| UMC107-ERI | 6.3 kb | | | 6.3 kb | | | | | 6.3 kb | | | |
| UMC27-H | 4.5 kb | | | | | | | | | | | |
| UMC27-B | 6.5 kb | | | | | | | | | | | |
| tda37-B | 8.2 kb | | | | | | | | | | | |
| tda37-B | 6.5 kb | | | | | | | | | | | |
| UMC43-B | | 9.7 kb | | 9.7 kb | | | | | | 9.7 kb | | |
| UMC43-B | 7.3 kb | 7.3 kb | 7.3 kb | 7.3 kb | | | 7.3 kb | 7.3 kb | | 7.3 kb | 7.3 kb | 7.3 kb |
| UMC43-B | 5.7 kb | | | | | | | | | | | |
| UMC40-B | 7.2 kb | | | | | | | | | | | |
| UMC40-B | | | 4.3 kb | 4.3 kb | | | 4.3 kb | | | | 4.3 kb | 4.3 kb |
| UMC40-B | 4.0 kb | 4.0 kb | 4.0 kb | 4.0 kb | | | | 4.0 kb | 4.0 kb | 4.0 kb | | |
| BNL7.71-H | | | 10.6 kb | | | | | | | | 10.6 kb | 10.6 kb |
| BNL5.71-B | 11.3 kb | 11.3 kb | 11.3 kb | 11.3 kb | | | | | | | | 11.3 kb |
| BNL5.71-B | | 6.8 kb | | 6.8 kb | | | | | 6.8 kb | | | |
| BNL5.71-B | 5.7 kb | | 5.7 kb | | | | 5.7 kb | 5.7 kb | | 5.7 kb | 5.7 kb | 5.7 kb |
| tda62-B | 5.5 kb | 5.5 kb | 5.5 kb | | | | | | | 5.5 kb | | |
| UMC68-H | 6.0 kb | 6.0 kb | 6.0 kb | 6.0 kb | | | 6.0 kb | 6.0 kb | 6.0 kb | | 6.0 kb | 6.0 kb |
| UMC104-H | | | | 12.4 kb | | | | | | | | |
| UMC104-H | 11.6 kb | | 11.6 kb | | | | | | | | | |
| UMC104-H | | 7.5 kb | | | | | | | | | | |
| UMC104-B | 9.4 kb | | 9.4 kb | 9.4 kb | 9.4 kb | 9.4 kb | | | | | | |
| phi10017-B | | | 15.1 kb | | | | | | | | | |
| phi10017-B | 9.5 kb | 9.5 kb | 9.5 kb | 9.5 kb | | | 9.5 kb | 9.5 kb | 9.5 kb | 9.5 kb | | |
| Chromosome 6 | | | | | | | | | | | | |
| tda50-B | 8.5 kb | 8.5 kb | 8.5 kb | 8.5 kb | | | | 8.5 kb | 8.5 kb | 8.5 kb | 8.5 kb | 8.5 kb |
| npi373-H | 6.5 kb | | 6.5 kb | | | | 6.5 kb | 6.5 kb | | 6.5 kb | 6.5 kb | 6.5 kb |
| npi373-H | | 5.6 kb | | 5.6 kb | | | 5.6 kb | 5.6 kb | 5.6 kb | | | |
| npi373-H | 3.0 kb | | | | | | | | | | | |
| tda204-B | | | 4.0 kb | | | | 4.0 kb | 4.0 kb | | | | 4.0 kb |
| NPI393-ERI | 12.1 kb | | 12.1 kb | | | | 12.1 kb | 12.1 kb | | 12.1 kb | 12.1 kb | |
| NPI393-ERI | 8.5 kb | 8.5 kb | 8.5 kb | 8.5 kb | | | | | 8.5 kb | | | 8.5 kb |
| NPI393-ERI | 5.6 kb | 5.6 kb | | | | | | | | | | |
| UMC65-H | 2.9 kb | | | | | | | | | | | |
| UMC46-ERI | 6.5 kb | | 6.5 kb | 6.5 kb | 6.5 kb | 6.5 kb | | | | | | |
| UMC46-ERI | 5.6 kb | 5.6 kb | 5.6 kb | 5.6 kb | | | 5.6 kb | 5.6 kb | 5.6 kb | 5.6 kb | 5.6 kb | 5.6 kb |
| asg7-H | 6.3 kb | | | | | | | | | | | |
| UMC28-H | | | 15.8 kb | 15.8 kb | | | | | | | | |
| UMC28-H | | | 11.9 kb | 11.9 kb | | | | | | | | |
| UMC28-B | | | 7.6 kb | 7.6 kb | | | 7.6 kb | 7.6 kb | 7.6 kb | 7.6 kb | 7.6 kb | 7.6 kb |
| UMC28-B | | | 6.6 kb | 6.6 kb | | | 6.6 kb | | | | | |
| UMC134-ERI | 15.3 kb | | 15.3 kb | 15.3 kb | 15.3 kb | 15.3 kb | | | | | | |
| UMC134-H | 7.5 kb | | 7.5 kb | 7.5 kb | 7.5 kb | 7.5 kb | | | | | | |
| UMC134-H | 4.7 kb | 4.7 kb | | 4.7 kb | | | | | 4.7 kb | | | |
| Chromosome 7 | | | | | | | | | | | | |
| asg8-H | 10.8 kb | | 10.8 kb | | | | | 10.8 kb | | | | |
| asg8-H | | 8.4 kb | | | | | | | | | | |
| O2-ERI | 9.4 kb | | 9.4 kb | 9.4 kb | | | | | | | | |
| BNL15.40-H | 5.8 kb | 5.8 kb | 5.8 kb | | | | | | | | 5.8 kb | |
| UMC116-ERI | 9.5 kb | 9.5 kb | 9.5 kb | 9.5 kb | | | | | | | 9.5 kb | |
| UMC116-H | 15.3 kb | | | | | | | | | | | |
| UMC110-B | 10.6 kb | 10.6 kb | 10.6 kb | 10.6 kb | | | 10.6 kb | 10.6 kb | 10.6 kb | 10.6 kb | 10.6 kb | 10.6 kb |
| UMC110-B | 4.9 kb | 4.9 kb | 4.9 kb | 4.9 kb | | | 4.9 kb | 4.9 kb | | 4.9 kb | 4.9 kb | |
| BNL8.32-H | | | 8.9 kb | | | | 8.9 kb | | 8.9 kb | | | 8.9 kb |
| BNL8.32-H | 7.4 kb | | | | | | | | | | | |
| BNL8.32-H | | 7.1 kb | 7.1 kb | 7.1 kb | | | | | | | | |
| BNL14.07-ERI | | 6.4 kb | | 6.4 kb | | | | | | | | |
| UMC80-H | 7.9 kb | 7.9 kb | 7.9 kb | 7.9 kb | | | | | | | 7.9 kb | |
| UMC80-H | 2.4 kb | 2.4 kb | | 2.4 kb | | | | 2.4 kb | 2.4 kb | | | |
| BNL16.06-ERI | 6.8 kb | | 6.8 kb | | | | | 6.8 kb | 6.8 kb | | | 6.8 kb |
| phi20020-H | 7.8 kb | 7.8 kb | 7.8 kb | 7.8 kb | | | 7.8 kb | 7.8 kb | 7.8 kb | 7.8 kb | 7.8 kb | 7.8 kb |
| phi20020-H | 6.6 kb | | | | | | | | | | | |
| Chromosome 8 | | | | | | | | | | | | |
| npi114-H | | | 10.0 kb | 10.0 kb | | | | | | 10.0 kb | 10.0 kb | 10.0 kb |
| npi114-H | 8.8 kb | | 8.8 kb | 8.8 kb | | | | 8.8 kb | 8.8 kb | | | 8.8 kb |
| npi114-H | | | 6.3 kb | | | | | | | | | 6.3 kb |
| BNL9.11-H | | 3.4 kb | | | | | | | | | | |
| UMC103-H | | 6.9 kb | 6.9 kb | 6.9 kb | | | 6.9 kb | 6.9 kb | 6.9 kb | 6.9 kb | 6.9 kb | 6.9 kb |
| UMC103-H | 5.7 kb | | | | | | | | | | | |
| UMC124-H | | | 8.0 kb | 8.0 kb | 8.0 kb | 8.0 kb | | | | | | |
| UMC124-H | 7.0 kb | | 7.0 kb | | | 7.0 kb | | | | | | |

TABLE 4-continued

De Novo Alleles in *Tripsacum -diploperennis* Hybrids and Maize X *Tripsacum - diploperennis*

| | *Tripsacum -diploperennis* Hybrids | | | | Maize X *Tripsacum - diploperennis* | | | | | | | |
|---|---|---|---|---|---|---|---|---|---|---|---|---|
| Probe/Enzyme | Sun Dance | 20A | Tripsacorn | Sun Star | 64SS | 64TC | 2019 | 3024 | 3028 | 3125 | 4126 | TC64 |
| UMC124-B | 21.0 kb | | 21.0 kb | 21.0 kb | 21.0 kb | 21.0 kb | | | | | | |
| UMC124-B | 19.0 kb | | 19.0 kb | 19.0 kb | 19.0 kb | 19.0 kb | | | | | | |
| UMC124-B | | | 6.6 kb | 6.6 kb | | | | | | | | |
| UMC124-B | | 2.6 kb | 2.6 kb | 2.6 kb | | | 2.6 kb | 2.6 kb | | | | 2.6 kb |
| UMC124-B | 1.6 kb | 1.6 kb | 1.6 kb | 1.6 kb | | | 1.6 kb | 1.6 kb | 1.6 kb | 1.6 kb | 1.6 kb | 1.6 kb |
| UMC120-H | | | 8.0 kb | 8.0 kb | 8.0 kb | 8.0 kb | | | | | | |
| UMC120-H | 3.2 kb | | 3.2 kb | 3.2 kb | | | 3.2 kb | | 3.2 kb | 3.2 kb | 3.2 kb | 3.2 kb |
| UMC120-H | 2.3 kb | | | | | | | | | | | |
| UMC120-H | | 1.4 kb | 1.4 kb | 1.4 kb | | | | | | | | 1.4 kb |
| UMC120-B | | | 23.1 | | | | | | | | | |
| UMC89-ERI | | | | 7.3 kb | | | | | | | | |
| UMC89-H | | | | 7.3 kb | | | | | | | | |
| UMC89-B | | | 9.5 kb | 9.5 kb | 9.5 kb | | 9.5 kb | 9.5 kb | | | | 9.5 kb |
| UMC89-B | | 6.0 kb | | 6.0 kb | | | | | 6.0 kb | | | |
| UMC89-B | 5.2 kb | | 5.2 kb | | | | | | | 5.2 kb | 5.2 kb | 5.2 kb |
| UMC89-B | 4.5 kb | | 4.5 kb | 4.5 kb | | | | | | 4.5 kb | 4.5 kb | 4.5 kb |
| BNL12.30-ERI | | 3.5 kb | | | | | | | | | | |
| UMC48-H | | | | 4.7 kb | | | 4.7 kb | | 4.7 kb | | | |
| UMC48-H | | | 3.5 kb | 3.5 kb | | | 3.5 kb | 3.5 kb | | | | 3.5 kb |
| UMC48-H | 2.2 kb | | | | | | | | | | | |
| UMC53-ERI | | 3.8 kb | 3.8 kb | 3.8 kb | | | 3.8 kb | 3.8 kb | | | | 3.8 kb |
| UMC53-ERI | 3.0 kb | | | | | | | | | | | |
| npi268-B | 6.4 kb | 6.4 kb | 6.4 kb | 6.4 kb | | | 6.4 kb | 6.4 kb | 6.4 kb | 6.4 kb | 6.4 kb | 6.4 kb |
| UMC3-ERI | 2.5 kb | | 2.5 kb | 2.5 kb | | | 2.5 kb | 2.5 kb | | 2.5 kb | 2.5 kb | 2.5 kb |
| UMC3-ERI | 2.0 kb | 2.0 kb | | 2.0 kb | | | | | | | | |
| Chromosome 9 | | | | | | | | | | | | |
| phi10005-ERI | 15.0 kb | 15.0 kb | 15.0 kb | 15.0 kb | | | 15.0 kb | 15.0 kb | 15.0 kb | 15.0 kb | 15.0 kb | |
| UMC113-ERI | 5.9 kb | | | | | | | | | | | |
| UMC113-ERI | | | 5.4 kb | 5.4 kb | | | | | | | | |
| UMC113-B | | | 12.8 kb | | | | | | | | | |
| UMC113-B | | 11.8 kb | | | | | | | | | | |
| UMC113-B | 10.5 kb | 10.5 kb | 10.5 kb | 10.5 kb | | | 10.5 kb | 10.5 kb | 10.5 kb | 10.5 kb | 10.5 kb | 10.5 kb |
| UMC192-H | 11.4 kb | 11.4 kb | 11.4 kb | 11.4 kb | | | 11.4 kb | 11.4 kb | 11.4 kb | 11.4 kb | 11.4 kb | 11.4 kb |
| UMC192-H | | 6.4 kb | | 6.4 kb | | | | | 6.4 kb | | | |
| wx-H | 21.0 kb | | | 21.0 kb | | | | | | | | |
| CSU147-H | 5.9 kb | 5.9 kb | | 5.9 kb | | | | | | | | |
| BNL5.10-H | 6.1 kb | 6.1 kb | | 6.1 kb | | | | | | | 6.1 kb | |
| BNL5.10-H | 4.4 kb | | | 4.4 kb | | | | | | | | |
| UMC114-B | 15.0 kb | | 15.0 kb | 15.0 kb | | | | | | | | |
| UMC114-B | | | 12.6 kb | | | | | | | | 12.6 kb | |
| UMC114-B | 11.5 kb | | | 11.5 kb | | | | | | | | |
| UMC114-B | | | 10.0 kb | 10.0 kb | | | 10.0 kb | 10.0 kb | | 10.0 kb | | 10.0 kb |
| UMC114-B | 8.8 kb | 8.8 kb | | 8.8 kb | | | | | 8.8 kb | | | |
| UMC114-B | | | 7.5 kb | 7.5 kb | | | | 7.5 kb | | 7.5 kb | | |
| UMC114-B | 6.5 kb | 6.5 kb | | 6.5 kb | | | | | | | | |
| UMC95-ERI | 13.3 kb | | 13.3 kb | | 13.3 kb | | | | | | | |
| UMC95-ERI | 5.6 kb | | 5.6 kb | | | | | | | | | |
| UMC95-H | | | 7.7 kb | | | | | | 7.7 kb | | | |
| UMC95-H | 4.8 kb | 4.8 kb | 4.8 kb | | | | 4.8 kb | | 4.8 kb | | | |
| UMC95-H | | | 4.1 kb | 4.1 kb | | | 4.1 kb | 4.1 kb | 4.1 kb | 4.1 kb | 4.1 kb | 4.1 kb |
| UMC95-B | | | 15.0 kb | 15.0 kb | | | | | | | | |
| UMC95-B | | | 9.0 kb | 9.0 kb | | | | | | | | |
| CSU61-ERI | 8.1 kb | 8.1 kb | 8.1 kb | 8.1 kb | | | 8.1 kb | 8.1 kb | 8.1 kb | | 8.1 kb | 8.1 kb |
| CSU61-ERI | 4.8 kb | | 4.8 kb | | | | | | | 4.8 kb | | 4.8 kb |
| BNL7.57-ERI | | | | | | | | | | | | |
| BNL7.57-B | | | | | | | | | | | | |
| BNL7.57-B | | | | | | | | | | | | |
| BNL7.57-B | | | | | | | | | | | | |
| BNL7.57-B | | | | | | | | | | | | |
| CSU54-ERI | 14.7 kb | 14.7 kb | | 14.7 kb | | | | | 14.7 kb | | | |
| CSU54-ERI | | | 12.6 kb | | | | | | 12.6 kb | 12.6 kb | 12.6 kb | 12.6 kb |
| BNL7.57-B | 1.0 kb | | | 1.0 kb | | | | | | | | |
| BNL7.57-B | | 11.6 kb | | | | | | | | | | |
| BNL7.57-B | | | 5.9 kb | 5.9 kb | | | 5.9 kb | 5.9 kb | 5.9 kb | | | |
| BNL7.57-B | 5.5 kb | | | | | | | | | | | |
| BNL7.57-B | 1.3 kb | | | | | | | | | | | |
| npi97-H | 3.9 kb | | | 3.9 kb | | | 3.9 kb | 3.9 kb | 3.9 kb | 3.9 kb | | |
| Chromosome 10 | | | | | | | | | | | | |
| phi20075-ERI | 7.1 kb | 7.1 kb | | 7.1 kb | | | | | 7.1 kb | | | |
| npi285-ERI | 15.3 kb | | 15.3 kb | | | | | | | | | |
| npi285-ERI | 12.4 kb | | 12.4 kb | | | | | | | 12.4 kb | 12.4 kb | |

TABLE 4-continued

De Novo Alleles in *Tripsacum -diploperennis* Hybrids and Maize X *Tripsacum - diploperennis*

| | *Tripsacum -diploperennis* Hybrids | | | | Maize X *Tripsacum - diploperennis* | | | | | | | |
|---|---|---|---|---|---|---|---|---|---|---|---|---|
| Probe/Enzyme | Sun Dance | 20A | Tripsacorn | Sun Star | 64SS | 64TC | 2019 | 3024 | 3028 | 3125 | 4126 | TC64 |
| npi285-ERI | 9.4 kb | | | | | | | | | | | |
| npi285-ERI | | 6.0 kb | | 6.0 kb | | | | | | 6.0 kb | | |
| KSU5-ERI | 9.8 kb | 9.8 kb | | 9.8 kb | | | | | | | | |
| KSU5-ERI | | 7.6 kb | | | | | | | | | | |
| KSU5-ERI | | 6.1 kb | | | | | | | | | | |
| KSU5-ERI | | 3.8 kb | | | | | | | | | | |
| KSU5-ERI | 3.5 kb | | 3.5 kb | | | | | | | 3.5 kb | 3.5 kb | 3.5 kb |
| UMC130-ERI | | 13.5 kb | | 13.5 kb | | | | | | | | |
| UMC130-ERI | 7.0 kb | | 7.0 kb | 7.0 kb | | | 7.0 kb | 7.0 kb | 7.0 kb | 7.0 kb | 7.0 kb | 7.0 kb |
| UMC130-H | 4.8 kb | | 4.8 kb | 4.8 kb | | | 4.8 kb | 4.8 kb | 4.8 kb | 4.8 kb | 4.8 kb | 4.8 kb |
| UMC130-H | 3.2 kb | | 3.2 kb | 3.2 kb | | | | | | 3.2 kb | | |
| UMC130-B | 3.2 kb | | | | | | | | | | | |
| UMC152-H | 12.4 kb | | | | | | | | | | | |
| UMC152-H | 7.1 kb | | 7.1 kb | | | | | | | 7.1 kb | 7.1 kb | |
| UMC152-H | | 5.6 kb | 5.6 kb | 5.6 kb | | | 5.6 kb | 5.6 kb | 5.6 kb | | | 5.6 kb |
| UMC64-H | 3.3 kb | | 3.3 kb | | | | | | | | | |
| phi06005 | 12.8 kb | | 12.8 kb | 12.8 kb | | | 12.8 kb | 12.8 kb | | 12.8 kb | 12.8 kb | 12.8 kb |
| UMC163-H | | 12.0 kb | 12.0 kb | | | | | | | | | |
| UMC163-H | 7.0 kb | | | 7.0 kb | | | | | 7.0 kb | | | |
| UMC163-H | | 4.8 kb | 4.8 kb | 4.8 kb | | | 4.8 kb | 4.8 kb | 4.8 kb | 4.8 kb | 4.8 kb | |
| UMC44-H | | 9.8 kb | | | | | | | | | | |
| UMC44-H | | | 8.7 kb | 8.7 kb | | | | | | | 8.7 kb | 8.7 kb |
| UMC44-H | 7.2 kb | 7.2 kb | | | | | | | | | | |
| UMC44-H | | | 5.5 kb | 5.5 kb | 5.5 kb | 5.5 kb | | | | 5.5 kb | 5.5 kb | 5.5 kb |
| UMC44-H | 4.0 kb | | | | | | | | | | | |
| BNL10.13-H | 10.8 kb | 10.8 kb | 10.8 kb | 10.8 kb | | | | | 10.8 kb | | | |
| npi306-H | | | | 7.0 kb | | | | | | | | |
| Mitochondria | | | | | | | | | | | | |
| pmt1-H | | | | 2.3 kb | | | | | | | | |
| pmt2-H | 8.0 kb | 8.0 kb | 8.0 kb | 8.0 kb | | | | | | | | 8.0 kb |
| pmt2-H | | 4.2 kb | | | | | | | | | | |
| pmt2-H | 2.8 kb | 2.8 kb | 2.8 kb | 2.8 kb | | | | | | 2.8 kb | 2.8 kb | 2.8 kb |
| pmt2-H | 2.1 kb | | | | | | | | | | | |
| pmt5-H | 12.3 kb | 12.3 kb | 12.3 kb | 12.3 kb | | | | | | | | |
| pmt5-H | | 8.1 kb | | | | | | | | | | |
| pmt5-H | | 3.2 kb | | 3.2 kb | | | | | | | | |
| pmt5-H | 2.5 kb | | 2.5 kb | 2.5 kb | | | | | | | | 2.5 kb |
| Locus Unknown | | | | | | | | | | | | |
| tda16-H | | | | 4.3 kb | | | | | | | | |
| tda17-H | 7.0 kb | 7.0 kb | 7.0 kb | | | | 7.0 kb | 7.0 kb | 7.0 kb | 7.0 kb | 7.0 kb | 7.0 kb |
| tda37-B | 8.2 kb | | | | | | | | | | | |
| tda37-B | 6.5 kb | | | | | | | | | | | |
| tda48-H | | | 8.2 kb | 8.2 kb | | | | | | | | |
| tda53-H | 3.8 kb | | | | | | | | | | | |
| tda53-H | 2.2 kb | 2.2 kb | 2.2 kb | 2.2 kb | | | 2.2 kb | 2.2 kb | | 2.2 kb | 2.2 kb | 2.2 kb |

TABLE 5

Novel Tripsacum Alleles in *Tripsacum -diploperennis* Hybrids and Maize X *Tripsacum -diploperennis*

| | *Tripsacum -diploperennis* Hybrids | | | | Maize X *Tripsacum - diploperennis* | | | | | | | |
|---|---|---|---|---|---|---|---|---|---|---|---|---|
| Probe/Enzyme | Sun Dance | 20A | Tripsacorn | Sun Star | 64SS | 64TC | 2019 | 3024 | 3028 | 3125 | 4126 | TC64 |
| Chromosome 2 | | | | | | | | | | | | |
| UMC53-ERV | 8.4 kb | | 8.4 kb | 8.4 kb | | | | | | 8.4 kb | 8.4 kb | |
| Chromosome 3 | | | | | | | | | | | | |
| UMC50-B | 7.8 kb | 7.8 kb | | | | | | | | | | |
| UMC50-B | 5.8 kb | | 5.8 kb | 5.8 kb | | | 5.8 kb | 5.8 kb | | 5.8 kb | 5.8 kb | 5.8 kb |
| UMC42-H | 7.6 kb | | 7.6 kb | | | | | | | | | |
| Chromosome 4 | | | | | | | | | | | | |
| phi20725-ERI | 9.7 kb | | | | | | 9.7 kb | | 9.7 kb | | | |
| npi386-H | | 12.6 kb | 12.6 kb | 12.6 kb | | | 12.6 kb | 12.6 kb | | | 12.6 kb | 12.6 kb |
| UMC42-H | 7.6 kb | | | 7.6 kb | | | | | | | | |
| tda62-B | 4.8 kb | 4.8 kb | | | | | | 4.8 kb | | 4.8 kb | 4.8 kb | 4.8 kb |

TABLE 5-continued

Novel Tripsacum Alleles in *Tripsacum -diploperennis* Hybrids and Maize X *Tripsacum -diploperennis*

| | Tripsacum -diploperennis Hybrids | | | | Maize X Tripsacum - diploperennis | | | | | | | |
|---|---|---|---|---|---|---|---|---|---|---|---|---|
| Probe/Enzyme | Sun Dance | 20A | Tripsacorn | Sun Star | 64SS | 64TC | 2019 | 3024 | 3028 | 3125 | 4126 | TC64 |
| Chromosome 5 | | | | | | | | | | | | |
| UMC90-H | | 7.8 kb | 7.8 kb | 7.8 kb | | | 7.8 kb | 7.8 kb | 7.8 kb | 7.8 kb | | 7.8 kb |
| UMC27-H | 8.3 kb | | 8.3 kb | 8.3 kb | | | 8.3 kb | 8.3 kb | 8.3 kb | 8.3 kb | 8.3 kb | 8.3 kb |
| Chromosome 6 | | | | | | | | | | | | |
| NPI393-ERI | 7.0 kb | 7.0 kb | | | | | | | | | | |
| UMC28-B | | | 10.0 kb | | | | | | | | 10.0 kb | |
| Chromosome 7 | | | | | | | | | | | | |
| asg8-H | | | | 8.7 kb | | | | | | | | |
| UMC110-B | 3.9 kb | | | | | | | | 3.9 kb | 3.9 kb | 3.9 kb | |
| UMC80-H | 10.6 kb | 10.6 kb | 10.6 kb | 10.6 kb | | | 10.6 kb | 10.6 kb | 10.6 kb | 10.6 kb | 10.6 kb | 10.6 kb |
| UMC80-H | 8.2 kb | 8.2 kb | 8.2 kb | 8.2 kb | | | | | | | 8.2 kb | |
| BNL6.06-ERI | 1.9 kb | | 1.9 kb | | | | | | | | | |
| Chromosome 8 | | | | | | | | | | | | |
| UMC48-H | | 6.2 kb | | 6.2 kb | | | | | 6.2 kb | | | |
| UMC53-ERV | 8.4 KB | | 8.4 KB | 8.4 KB | | | | | | 8.4 KB | 8.4 KB | |
| Chromosome 10 | | | | | | | | | | | | |
| UMC163-H | 2.6 kb | | | | | | | | 2.6 kb | | | |
| Mitochondria | | | | | | | | | | | | |
| pmt5-H | 3.6 kb | 3.6 kb | 3.6 kb | 3.6 kb | | | 3.6 kb | 3.6 kb | 3.6 kb | 3.6 kb | 3.6 kb | 3.6 kb |
| Locus Unknown | | | | | | | | | | | | |
| tda168-ERI | 3.6 kb | | | 3.6 kb | | | | | | | | |

Deposit of Seeds

A sample comprising at least 2500 seeds derived from crosses between *Tripsacum dactyloides* and *Zea diploperennis* as described herein were deposited with American Type Culture Collection, 12301 Parklawn Drive, Rockville, Md. 20852 on Aug. 28, 1992. The accession number is ATCC75297.

The present invention is not limited in scope by the seeds deposited, since the deposited embodiments are intended as illustrations of the invention and any seeds, cell lines, plant parts, plants derived from tissue culture or seeds which are functionally equivalent are within the scope of this invention. While the invention has been described in detail and with reference to specific embodiments thereof, it will be apparent to one skilled in the art that changes and modifications can be made without departing from the spirit and scope of the invention in addition to those shown and described herein. Such modifications are intended to fall within the scope of the appended claims.

I claim:

1. A method of screening a plant to determine whether the plant is a *Tripsacum daclyloides/Zea diploperennis* hybrid, said method comprising:
    isolating the total genomic DNA from said plant;
    digesting said genomic DNA with one to four of the restriction enzymes selected from the group consisting of EcoRI, EcoRV, HindIII and BamHI;
    probing said digested genomic DNA with one or more DNA markers selected from the group consisting of the maize nuclear DNA probes, maize mitochondrial DNA probes, and Tripsacum DNA probes recited below;
    and determining the presence of one or more of the following restriction fragments of the following fragment sizes, wherein said restriction fragments are characterized by the following molecular marker-restriction enzyme associations and the associated fragment sizes selected from the group consisting of:
    BNL5.62, EcoRI, 10.3 kb; npi97, HindIII, 3.9 kb; UMC157, EcoRI, 6.5 kb and 3.3 kb; UMC157, HindIII, 5.5 kb; UMC157 BamHI, 14.0 kb, 8.6 kb and 4.5 kb; UMC11, BamHI, 7.0 kb; CSU3, BamHI, 10.0 kb, 7.6 kb and 3.5 kb; UMC67, EcoRI, 19.2 kb; UMC67, BamHI, 13.4 kb and 1.6 kb; CSU92, BamHI, 13.3 kb and 7.5 kb; 62 BamHI, 12.7 kb, 9.7 kb and 6.6 kb; UMC58, HindIII, 3.3 kb; CSU164, EcoRI, 9.0 kb and 7.0 kb; UMC128, HindIII, 6.0 kb; UMC107, EcoRI, 6.3 kb and 5.3 kb; UMC107, HindIII, 19.2 kb; UMC140, EcoRI, 5.0 kb; UMC140, HindIII, 6.5 kb; UMC107, EcoRI, 6.3 kb; adh1, HindIII, 9.4 kb; adh1, BamHI, 9.4 kb; UMC161, HindIII, 3.3 kb; BNL8.29, HindIII, 8.3 kb; UMC53, EcoRI, 9.4 kb, 3.8 kb and 3.0 kb; UMC53, EcoRV, 8.4 kb, 3.8 kb and 3.0 kb; UMC6, EcoRI, 3.8 kb; UMC6, HindIII, 9.4 kb; UMC6, BamHI, 13.2 kb, 12.7 kb, and 7.0 kb; UMC61, HindIII, 3.4 and 2.8 kb; UMC34, EcoRI, 7.5 kb and 5.4 kb; UMC34, HindIII, 8.8 kb, 6.5 kb and 5.8 kb; UMC135, HindIII, 11.6 kb and 10.8 kb; UMC131, EcoRI, 10.6 kb, 5.8 kb and 4.3 kb; UMC55, EcoRI, 3.9 kb; UMC55, HindIII, 4.3 kb; UMC5, EcoRI, 5.4 kb; UMC5, HindIII, 6.5 kb; UMC49, BamHI, 8.2kb, 6.0 kb, 4.2 kb, and 3.2 kb; UMC36, BamIII, 4,2 kb; UMC32, HindIII, 6.7 kb; asg24, HindIII, 7.2 kb and 6.4 kb; UMC121, EcoRI, 3.7 kb and 3.2 kb; BNL8.35, HindIII, 9.9 kb and 8.7 kb; UMC50, BamHI, 7.8 kb, 6.8 kb, 5.8 kb and 3.8 kb; UMC42, HindIII, 10.4 kb, 8.9 kb, 7.6 kb, 3.7 kb and 3.0 kb; npi247, EcoRI, 8.0 kb; npi247, HindIII, 3.0 kb; UMC10, HindIII, 5.9 kb and 3.0 kb; UMC10, EcoRI, 6.5 kb and 5.5 kb; UMC102, EcoRI, 2.7 kb; BNL6.06, EcoRI, 6.8 kb; BNL5.37, HindIII, 10.3 kb, 5.8 kb and 3.5 kb; npi296, EcoRI, 7.9 kb; UMC3, EcoRI, 2.5 kb and 2.0 kb; npi212, HindIII, 4.3 kb; npi212, BamHI, 5.4 kb; UMC39, EcoRI, 12.2 kb, 9.2kb, 7.8 kb and 7.1 kb UMC63, HindIII, 9.5 kb and 4.3 kb; UMC96, HindIII, 11.8 kb, 6.4 kb and 5.5 kb; UMC96, BamHI, 7.5 kb; UMC2, EcoRI, 11.8 kb, 10.4 kb and 8.0 kb; CSU25, HindIII, 4.5 and 4.3 kb; agrr115, EcoRI, 8.0 kb and 5.4 kb; agrr115, BamHI, 5.4 kb and 3.5 kb, phi20725, EcoRI, 10.3 kb, 9.7 kb and 7.2 kb; phi20725, HindIII, 1.5 kb; UMC31, EcoRI, 5.8 kb; UMC31, BamHI 6.5 kb; BNL5.46, HindIII, 13.7 kb, 10.5 kb, 9.7 kb and 5.1 kb; npi386, HindIII, 12.6 kb, 9.3 kb and 8.2 kb; tda62, BamHI, 5.5 kb and 4.8 kb; BNL5.71, EcoRI, 11.3 kb, 6.8 kb, and 5.7 kb; BNL5.71, BamHI, 11.3 kb, 6.8 kb and 5.7 kb; UMC156, HindIII, 3.0 kb; UMC66, EcoRI, 10.5 kb and 6.5 kb; UMC66, BamHI, 3.7 kb; UMC19, BamHI, 12.3 kb; UMC104, HindIII, 12.4 kb, 11.6 kb and 7.5 kb; UMC104, BamHI, 9.4 kb; UMC133, HindIII, 10.6 kb, 9.9 kb, 9.2 kb and 7.7 kb; UMC52, BamHI, 8.7 kb, 6.9 kb, 3.8 kb, 3.0 kb and 2.0 kb; BNL15.07, HindIII, 2.9 kb and 2.7 kb; npi409, EcoRI, 9.4 kb; npi409, HindIII, 10.4 kb, 9.0 kb and 3.9 kb; UMC147, HindIII, 16.3 kb, 3.8 kb and 2.4 kb; UMC90, HindIII, 7.8 kb, 2.8 kb and 2.5 kb; UMC90, BamHI, 9.0 kb; UMC27, HindIII, 8.3 and 4.5 kb; tda37, BamHI, 8.2 kb and 6.5 kb; UMC43, BamHI, 9.7 kb, 7.3 kb and 5.7 kb; UMC40, BamHI, 7.2 kb, 4.3 kb and 4.0; BNL7.71, HindIII, 10.6 kb; tda62, BamIII, 5.5 kb; UMC68, HindIII, 6.0 kb; phi10017, BamHI, 15.1 kb and 9.5 kb; tda50, BamHI, 8.5 kb; npi373, HindIII, 6.5 kb, 5.6 kb and 3.0 kb; tda204, BamHI, 4.0 kb; npi393, EcoRI, 12.1 kb, 8.5 kb, 7,0 kb and 5.6 kb; UMC65, HindIII, 2.9 kb; UMC46, EcoRI, 6.5 kb and 5.6 kb; asg7, HindIII, 6.3 kb; UMC28, HindIII, 15.8 kb and 11.9 kb; UMC28, BamHI, 10.0 kb, 7.6 kb and 6.6 kb; UMC134, BamHI, 4.7 kb; UMC134, HindIII, 7.5 kb; asg8, HindIII, 10.8 kb, 8,7 kb and 8.4 kb; O2, EcoRI, 9.4 kb; BNL15.40, HindIII, 5.8 kb; UMC116, EcoRI, 9.5 kb; UMC110, BamHI, 10.6 kb, 4.9 kb and 3.9 kb; BNL8.32, HindIII, 8.9 kb, 7.4 kb and 7.1 kb; BNL14.07, EcoRI, 6.4 kb, UMC80, HindIII, 10.6 kb, 8.2 kb and 2.4 kb; BNL16.06, EcoRI, 6.8 kb and 1.9 kb; phi20020, HindIII, 7.8 kb and 6.6 kb; npi114, HindIII, 10.0 kb, 8.8 kb and 6.3 kb; BNL9.11, HindIII, 3.4 kb; UMC103, HindIII, 6.9 kb and 5.7 kb; UMC124, HindIII, 8.0 and 7.0; UMC124, BamHI, 6.6 kb and 2.6 kb; UMC120, HindIII, 3.2 kb, 2.3 kb and 1.4 kb; UMC89, EcoRI, 7.3 kb; UMC89, HindIII, 7.3 kb; UMC89, BamHI, 9.5 kb, 6.0 kb, 5.2 kb and 4.5 kb; BNL12.30, EcoRI, 3.5 kb; UMC48, HindIII, 6.2 kb, 5.3 kb, 4.7 kb, 3.5 kb and 2.2 kb; npi268, BamHI, 6.4 kb; phi10005, EcoRI, 15.0 kb; UMC113, EcoRI, 5.9 kb and 5.4 kb; UMC113, BamHI, 12.8 kb, 11.8 kb and 10.5 kb; UMC192, HindIII, 11.4 kb and 6.4 kb; wx(waxy), HindIII, 21.0 kb; CSU147, HindIII, 5.9 kb; BNL5.10, HindIII, 6.1 kb and 4.4 kb; UMC114, BamHI, 12.6 kb, 11.5 kb, 10.0 kb, 8.8 kb, 7.5 kb and 6.5 kb; UMC95, EcoRI, 5.6 kb; UMC95, HindIII, 7.7 kb, 4.8 kb and 4.1 kb; UMC95, BamHI, 15.0 kb and 9.0 kb; CSU61, EcoRI, 8.1 kb and 4.8 kb; BNL7.57, EcoRI, 1.0 kb; BNL7.57, BamHI, 11.6 kb, 5.9 kb and 1.3 kb; CSU54, EcoRI, 14.7 kb and 12.6 kb; phi20075, EcoRI, 7.1 kb; npi285, EcoRI, 12.4 kb, 9.4 kb and 6.0 kb; KSU5, EcoRI, 9.8 kb, 7.6 kb, 6.1 kb, 3.8 kb and 3.5 kb; UMC130, EcoRI, 13.5 kb and 7.0 kb; UMC130, HindIII, 4.8 kb and 3.2 kb; UMC130, BamIII, 3.2 kb; UMC152, HindIII, 12.4, 7.1 kb and 5.6 kb; UMC64, HindIII, 3.3 kb; phi06005, EcoRI, 12.8 kb; UMC163, HindIII, 7.0 kb, 4.8 kb and 2.6 kb; UMC44, HindIII, 9.8 kb, 8.7 kb, 7.2 kb, 5.5 kb and 4.0 kb; BNL10.13, HindIII, 10.8 kb; npi306, HindIII, 7.0 kb; pmt1, HindIII, 2.3 kb; pmt2, HindIII, 8.0 kb, 4.2 kb, 2.8 kb and 2.1 kb; pmt5, HindIII, 12.3 kb, 8.1 kb, 3.6 kb, 3.2 kb and 2.5 kb; tda48, HindIII, 8.2 kb; tda53, HindIII, 3.8 kb and 2.2 kb; tda168, EcoRI, 3.6 kb; tda16, HindIII, 4.3 kb; and tda17, HindIII, 7.0 kb.

\* \* \* \* \*